United States Patent
MacPherson

(10) Patent No.: US 12,371,694 B2
(45) Date of Patent: Jul. 29, 2025

(54) COMPOSITIONS AND METHODS FOR THE SYNTHESIS AND IDENTIFICATION OF COVALENT APTAMERS

(71) Applicant: University of Hawaii, Honolulu, HI (US)

(72) Inventor: Iain Seido MacPherson, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 1079 days.

(21) Appl. No.: 17/289,767

(22) PCT Filed: Nov. 13, 2019

(86) PCT No.: PCT/US2019/061096
§ 371 (c)(1),
(2) Date: Apr. 29, 2021

(87) PCT Pub. No.: WO2020/102287
PCT Pub. Date: May 22, 2020

(65) Prior Publication Data
US 2021/0395742 A1 Dec. 23, 2021

Related U.S. Application Data

(60) Provisional application No. 62/767,363, filed on Nov. 14, 2018.

(51) Int. Cl.
*C12N 15/115* (2010.01)
*C07H 19/10* (2006.01)
*C07H 21/04* (2006.01)
*C12N 15/10* (2006.01)

(52) U.S. Cl.
CPC .......... *C12N 15/115* (2013.01); *C07H 19/10* (2013.01); *C07H 21/04* (2013.01); *C12N 15/1048* (2013.01); *C12N 2310/16* (2013.01); *C12N 2310/314* (2013.01); *C12N 2310/3513* (2013.01)

(58) Field of Classification Search
CPC .............. C12N 15/115; C12N 15/1048; C12N 2310/16; C12N 2310/314; C12N 2310/3513; C07H 19/10; C07H 21/04; C07H 21/00; C07H 19/073
See application file for complete search history.

(56) References Cited

U.S. PATENT DOCUMENTS

2014/0100120 A1* 4/2014 Gorenstein .......... C12N 15/115 506/4

FOREIGN PATENT DOCUMENTS

| WO | WO-2014047357 A1 * | 3/2014 | ............. A61K 47/68 |
|----|---------------------|--------|--------------------------|
| WO | WO-2014047375 A1 * | 3/2014 | ............. E21B 21/08 |
| WO | 2016005474 A1 | 1/2016 | |
| WO | 2017053905 A1 | 3/2017 | |
| WO | 2018152470 A1 | 8/2018 | |

OTHER PUBLICATIONS

Miyakawa et al. "Structural and molecular basis for hyperspecificity of RNA aptamer to human immunoglobulin G" (RNA (2008) 14(6):1154-63). (Year: 2008).*
Diafa, S. et al. (2015) "Generation of aptamers with an expanded chemical repertoire," Molecules 20(9):16643-16671.
He, W. et al. (2012) "X-Aptamers: A bead-based selection method for random incorporation of drug-like moieties onto next-generation aptamers for enhanced binding," Biochemistry 51(42):8321-8323.
International Search Report and Written Opinion in PCT/US2019/061096 dated Apr. 7, 2020.
MacPherson, I.S. et al. (2018) "Chemically 'barbed' aptamers selected from a base-modified RNA library," Aptamers 2:74-81.
Pfeiffer, F. et al. (2018) "Identification and Characterization of nucleobase-modified aptamers by click-SELEX," Nature Protocols 13(5):1153-1180.
Smith, D. et al. (2003) "Sensitivity and specificity of photoaptamer probes," Mol. Cell. Proteom. 2:11-18.
Temme, J.S. et al. (2013) "Directed Evolution of 2G12-Targeted Nonamannose Glycoclusters by SELMA," Chemistry 19:17291-95.
Temme, J.S. et al. (2014) "High Temperature SELMA: Evolution of DNA-Supported Oligomannose Clusters Which Are Tightly Recognized by HIV bnAb 2G12," J. Am. Chem. Soc. 136:1726-29.
Temme, J.S. "SELMA: Selection with Modified Aptamers," Curr. Protoc. Chem. Biol. 7:73-92.
Van Buggenum, J.A.G.L. et al. (2016) "A covalent and cleavable antibody-DNA conjugation strategy for sensitive protein detection via immuno-PCR," Scientific Reports 6:22675.
International Preliminary Report on Patentability in PCT/US2019/061096 dated May 27, 2021.
Miyakawa, S., et al. (2008) "Structural and molecular basis for hyperspecificity of RNA aptamer to human Immunoglobulin G," RNA 14:1154-1163.

* cited by examiner

*Primary Examiner* — J. E. Angell
(74) *Attorney, Agent, or Firm* — Licata & Tyrrell P.C.; Jane Massey Licata

(57) ABSTRACT

Compositions and methods for preparing and identifying aptamers and aptamer-protein conjugates are provided. The use of a nucleotide analog functionalized with an amine-reactive cross-linker facilitates covalent cross-linking of the aptamer to a protein, in particular site-specific cross-linking to the Fc domain of an antibody.

6 Claims, 4 Drawing Sheets
Specification includes a Sequence Listing.

```
                              SEQUENCE LISTING

<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotie
<220> FEATURE:
<221> NAME/KEY: misc_feature
<222> LOCATION: (13)..(13)
<223> OTHER INFORMATION: N is U, dU, dT, 5-EU, EdU, 2'-modified EU,
      triazole-modified dU or triazole-modified U.
<220> FEATURE:
<221> NAME/KEY: misc_feature
<222> LOCATION: (17)..(17)
<223> OTHER INFORMATION: N is U, dU, dT, 5-EU, EdU, 2'-modified EU,
      triazole-modified dU or triazole-modified U.

<400> SEQUENCE: 1
agcgcggaac cgngccnggc                                                    20

<210> SEQ ID NO 2
<211> LENGTH: 16
<212> TYPE: DNA
<213> ORGANISM: Artificial Sequence
<220> FEATURE:
<223> OTHER INFORMATION: Synthetic oligonucleotie
<220> FEATURE:
<221> NAME/KEY: misc_feature
<222> LOCATION: (1)..(1)
<223> OTHER INFORMATION: N is U, dU, dT, 5-EU, EdU, 2'-modified EU,
      triazole-modified dU or triazole-modified U.
<220> FEATURE:
<221> NAME/KEY: misc_feature
<222> LOCATION: (9)..(9)
<223> OTHER INFORMATION: N is U, dU, dT, 5-EU, EdU, 2'-modified EU,
      triazole-modified dU or triazole-modified U.

<400> SEQUENCE: 2
naacgcarna agcgag                                                        16

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotie
<220> FEATURE:
<221> NAME/KEY: misc_feature
<222> LOCATION: (4)..(4)
<223> OTHER INFORMATION: N is U, dU, dT, 5-EU, EdU, 2'-modified EU,
      triazole-modified dU or triazole-modified U.
<220> FEATURE:
<221> NAME/KEY: misc_feature
<222> LOCATION: (12)..(12)
<223> OTHER INFORMATION: N is U, dU, dT, 5-EU, EdU, 2'-modified EU,
      triazole-modified dU or triazole-modified U.

<400> SEQUENCE: 3
caanggcaac angcacacag a                                                  21

<210> SEQ ID NO 4
<211> LENGTH: 18
<212> TYPE: DNA
<213> ORGANISM: Artificial Sequence
```

```
<220> FEATURE:
<223> OTHER INFORMATION: Synthetic oligonucleotie

<400> SEQUENCE: 4
ccgggctttg tgtcactt                                                    18

<210> SEQ ID NO 5
<211> LENGTH: 44
<212> TYPE: DNA
<213> ORGANISM: Artificial Sequence
<220> FEATURE:
<223> OTHER INFORMATION: Synthetic oligonucleotie

<400> SEQUENCE: 5
gctcgttctc cttccctctc ctatagtgag tcgtattaca gttg                       44

<210> SEQ ID NO 6
<211> LENGTH: 87
<212> TYPE: DNA
<213> ORGANISM: Artificial Sequence
<220> FEATURE:
<223> OTHER INFORMATION: Synthetic oligonucleotie
<220> FEATURE:
<221> NAME/KEY: misc_feature
<222> LOCATION: (19)..(43)
<223> OTHER INFORMATION: n is a, c, g, or t

<400> SEQUENCE: 6
ccgggctttg tgtcacttnn nnnnnnnnnn nnnnnnnnnn nnngctcgtt ctccttccct      60
ctcctatagt gagtcgtatt acagttg                                          87

<210> SEQ ID NO 7
<211> LENGTH: 28
<212> TYPE: DNA
<213> ORGANISM: Artificial Sequence
<220> FEATURE:
<223> OTHER INFORMATION: Synthetic oligonucleotie
<220> FEATURE:
<221> NAME/KEY: misc_feature
<222> LOCATION: (1)..(1)
<223> OTHER INFORMATION: biotinylation

<400> SEQUENCE: 7
caactgtaat acgactcact ataggaga                                         28

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotie
<220> FEATURE:
<221> NAME/KEY: modified_base
<222> LOCATION: (1)..(1)
<223> OTHER INFORMATION: 5'-methylisocytosine

<400> SEQUENCE: 8
cccgggcttt gtgtcactt                                                   19

<210> SEQ ID NO 9
<211> LENGTH: 124
<212> TYPE: DNA
<213> ORGANISM: Artificial Sequence
<220> FEATURE:
<223> OTHER INFORMATION: Synthetic oligonucleotie

<400> SEQUENCE: 9
```

```
gctcgttctc cttccctctc cttttttttt tcaacaccac agaccagtat acccagaaat    60
gacgcaagca tagacaaacg atttagacat gagtgcccca cacaacgaac aagcttttt   120 ttta                                                               124
```

<210> SEQ ID NO 10
<211> LENGTH: 28
<212> TYPE: DNA
<213> ORGANISM: Artificial Sequence
<220> FEATURE:
<223> OTHER INFORMATION: Synthetic oligonucleotie

<400> SEQUENCE: 10

```
caactgtaat acgactcact ataggaga                                      28
```

<210> SEQ ID NO 11
<211> LENGTH: 82
<212> TYPE: DNA
<213> ORGANISM: Artificial Sequence
<220> FEATURE:
<223> OTHER INFORMATION: Synthetic oligonucleotie

<400> SEQUENCE: 11

```
gcttgttcgt tgtgtggggc actcatgtct aaatcgtttg tctatgcttg cgtcatttct    60
gggtatactg gtctgtggtg aa                                            82
```

<210> SEQ ID NO 12
<211> LENGTH: 28
<212> TYPE: DNA
<213> ORGANISM: Artificial Sequence
<220> FEATURE:
<223> OTHER INFORMATION: Synthetic oligonucleotie

<400> SEQUENCE: 12

```
caactgtaat acgactcact ataggaga                                      28
```

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotie

<400> SEQUENCE: 13

```
ccgggctttg tgtcactt                                                 18
```

<210> SEQ ID NO 14
<211> LENGTH: 25
<212> TYPE: RNA
<213> ORGANISM: Artificial Sequence
<220> FEATURE:
<223> OTHER INFORMATION: Synthetic oligonucleotie
<220> FEATURE:
<221> NAME/KEY: modified_base
<222> LOCATION: (6)..(6)
<223> OTHER INFORMATION: 5-ethynyluridine
<220> FEATURE:
<221> NAME/KEY: modified_base
<222> LOCATION: (11)..(12)
<223> OTHER INFORMATION: 5-ethynyluridine
<220> FEATURE:
<221> NAME/KEY: modified_base
<222> LOCATION: (16)..(16)
<223> OTHER INFORMATION: 5-ethynyluridine
<220> FEATURE:
<221> NAME/KEY: modified_base
<222> LOCATION: (24)..(25)
<223> OTHER INFORMATION: 5-ethynyluridine

<400> SEQUENCE: 14
ccggguagcc uuaacugacg cgcuu                                    25

<210> SEQ ID NO 15
<211> LENGTH: 25
<212> TYPE: RNA
<213> ORGANISM: Artificial Sequence
<220> FEATURE:
<223> OTHER INFORMATION: Synthetic oligonucleotie
<220> FEATURE:
<221> NAME/KEY: modified_base
<222> LOCATION: (10)..(12)
<223> OTHER INFORMATION: 5-ethynyluridine
<220> FEATURE:
<221> NAME/KEY: modified_base
<222> LOCATION: (16)..(16)
<223> OTHER INFORMATION: 5-ethynyluridine
<220> FEATURE:
<221> NAME/KEY: modified_base
<222> LOCATION: (24)..(25)
<223> OTHER INFORMATION: 5-ethynyluridine

<400> SEQUENCE: 15
agggcaaaau uuaacugaca agcuu                                    25

<210> SEQ ID NO 16
<211> LENGTH: 24
<212> TYPE: RNA
<213> ORGANISM: Artificial Sequence
<220> FEATURE:
<223> OTHER INFORMATION: Synthetic oligonucleotie
<220> FEATURE:
<221> NAME/KEY: modified_base
<222> LOCATION: (5)..(5)
<223> OTHER INFORMATION: 5-ethynyluridine
<220> FEATURE:
<221> NAME/KEY: modified_base
<222> LOCATION: (10)..(12)
<223> OTHER INFORMATION: 5-ethynyluridine
<220> FEATURE:
<221> NAME/KEY: modified_base
<222> LOCATION: (16)..(16)
<223> OTHER INFORMATION: 5-ethynyluridine
<220> FEATURE:
<221> NAME/KEY: modified_base
<222> LOCATION: (24)..(24)
<223> OTHER INFORMATION: 5-ethynyluridine

<400> SEQUENCE: 16
aggguaaaau uuaacugaca agcu                                     24

<210> SEQ ID NO 17
<211> LENGTH: 25
<212> TYPE: RNA
<213> ORGANISM: Artificial Sequence
<220> FEATURE:
<223> OTHER INFORMATION: Synthetic oligonucleotie
<220> FEATURE:
<221> NAME/KEY: modified_base
<222> LOCATION: (1)..(1)
<223> OTHER INFORMATION: 5-ethynyluridine
<220> FEATURE:
<221> NAME/KEY: modified_base
<222> LOCATION: (11)..(12)
<223> OTHER INFORMATION: 5-ethynyluridine
<220> FEATURE:
<221> NAME/KEY: modified_base
<222> LOCATION: (16)..(16)
<223> OTHER INFORMATION: 5-ethynyluridine
<220> FEATURE:
<221> NAME/KEY: modified_base
<222> LOCATION: (24)..(25)

<223> OTHER INFORMATION: 5-ethynyluridine

<400> SEQUENCE: 17
uggaaacgca uuaacuaaca agcuu                           25

<210> SEQ ID NO 18
<211> LENGTH: 25
<212> TYPE: RNA
<213> ORGANISM: Artificial Sequence
<220> FEATURE:
<223> OTHER INFORMATION: Synthetic oligonucleotie
<220> FEATURE:
<221> NAME/KEY: modified_base
<222> LOCATION: (9)..(10)
<223> OTHER INFORMATION: 5-ethynyluridine
<220> FEATURE:
<221> NAME/KEY: modified_base
<222> LOCATION: (14)..(14)
<223> OTHER INFORMATION: 5-ethynyluridine
<220> FEATURE:
<221> NAME/KEY: modified_base
<222> LOCATION: (24)..(25)
<223> OTHER INFORMATION: 5-ethynyluridine

<400> SEQUENCE: 18
gggacagcuu aacugacgaa aacuu                           25

<210> SEQ ID NO 19
<211> LENGTH: 24
<212> TYPE: RNA
<213> ORGANISM: Artificial Sequence
<220> FEATURE:
<223> OTHER INFORMATION: Synthetic oligonucleotie
<220> FEATURE:
<221> NAME/KEY: modified_base
<222> LOCATION: (7)..(7)
<223> OTHER INFORMATION: 5-ethynyluridine
<220> FEATURE:
<221> NAME/KEY: modified_base
<222> LOCATION: (9)..(9)
<223> OTHER INFORMATION: 5-ethynyluridine
<220> FEATURE:
<221> NAME/KEY: modified_base
<222> LOCATION: (13)..(13)
<223> OTHER INFORMATION: 5-ethynyluridine
<220> FEATURE:
<221> NAME/KEY: modified_base
<222> LOCATION: (23)..(24)
<223> OTHER INFORMATION: 5-ethynyluridine

<400> SEQUENCE: 19
ggcacguaua acugacaaac gcuu                            24

<210> SEQ ID NO 20
<211> LENGTH: 25
<212> TYPE: RNA
<213> ORGANISM: Artificial Sequence
<220> FEATURE:
<223> OTHER INFORMATION: Synthetic oligonucleotie
<220> FEATURE:
<221> NAME/KEY: modified_base
<222> LOCATION: (2)..(2)
<223> OTHER INFORMATION: 5-ethynyluridine
<220> FEATURE:
<221> NAME/KEY: modified_base
<222> LOCATION: (10)..(11)
<223> OTHER INFORMATION: 5-ethynyluridine
<220> FEATURE:
<221> NAME/KEY: modified_base
<222> LOCATION: (16)..(17)
<223> OTHER INFORMATION: 5-ethynyluridine
<220> FEATURE:
<221> NAME/KEY: modified_base
<222> LOCATION: (21)..(21)
<223> OTHER INFORMATION: 5-ethynyluridine
<220> FEATURE:
<221> NAME/KEY: modified_base
<222> LOCATION: (23)..(23)
<223> OTHER INFORMATION: 5-ethynyluridine

<400> SEQUENCE: 20
auaacggcau ugagcuuaac uguaa                                              25

<210> SEQ ID NO 21
<211> LENGTH: 25
<212> TYPE: RNA
<213> ORGANISM: Artificial Sequence
<220> FEATURE:
<223> OTHER INFORMATION: Synthetic oligonucleotie
<220> FEATURE:
<221> NAME/KEY: modified_base
<222> LOCATION: (1)..(1)
<223> OTHER INFORMATION: 5-ethynyluridine
<220> FEATURE:
<221> NAME/KEY: modified_base
<222> LOCATION: (8)..(8)
<223> OTHER INFORMATION: 5-ethynyluridine
<220> FEATURE:
<221> NAME/KEY: modified_base
<222> LOCATION: (13)..(15)
<223> OTHER INFORMATION: 5-ethynyluridine
<220> FEATURE:
<221> NAME/KEY: modified_base
<222> LOCATION: (17)..(18)
<223> OTHER INFORMATION: 5-ethynyluridine
<220> FEATURE:
<221> NAME/KEY: modified_base
<222> LOCATION: (23)..(23)
<223> OTHER INFORMATION: 5-ethynyluridine

<400> SEQUENCE: 21
uagcaccuaa cauuucuuga aauga                                              25

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotie
<220> FEATURE:
<221> NAME/KEY: misc_feature
<222> LOCATION: (1)..(1)
<223> OTHER INFORMATION: n is a, c, g, or t

<400> SEQUENCE: 22
nmmmragcgc ggaaccgtgc ctggc                                              25

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotie

<400> SEQUENCE: 23
grcmrrrrrt aacgcartaa gcgag                                              25

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotie

```
<400> SEQUENCE: 24
agcgcggaac cgtgcctggc                                              20

<210> SEQ ID NO 25
<211> LENGTH: 16
<212> TYPE: DNA
<213> ORGANISM: Artificial Sequence
<220> FEATURE:
<223> OTHER INFORMATION: Synthetic oligonucleotie

<400> SEQUENCE: 25
taacgcarta agcgag                                                  16
```

COMPOSITIONS AND METHODS FOR THE SYNTHESIS AND IDENTIFICATION OF COVALENT APTAMERS

INTRODUCTION

This application is a U. S. National Stage Application of International Application Serial Number PCT/US2019/061096 filed Nov. 13, 2019 and claims benefit of priority to U.S. Provisional Patent Application Ser. No. 62/767,363, filed Nov. 14, 2018, the contents of which are incorporated herein by reference in their entirety.

BACKGROUND

Protein detection and quantification is essential in life sciences and clinical diagnostics. Detection and quantification of DNA is generally more sensitive than that of protein largely due to the ability to replicate it with polymerases. This ability has also enabled traditional Sanger sequencing and next generation sequencing technologies. Because of these inherent advantages, technologies have been developed that combine antibody-based recognition of proteins with DNA amplification, quantification and sequencing in the form of antibody-oligonucleotide conjugates. Among these is immuno-PCR, which allows highly sensitive quantification of proteins in a format that mirrors that of ELISA (Enzyme Linked Immunosorbant Assay) but differs in that the antibody is conjugated with an oligodeoxynucleotide instead of an enzyme. As a result, amplification of the oligodeoxynucleotide with quantitative PCR enables ultra-sensitive measurement of target protein concentrations. Proximity-based assays have also been developed for the detection and quantification of proteins, protein-protein interactions, and post-translational modifications. For protein measurement, proximity-based assays require two antibody-oligonucleotide conjugates that bind to non-overlapping epitopes on the target protein. Simultaneous binding by the antibodies brings their accompanying oligodeoxynucleotides into close proximity with one another. In proximity ligation, the increased local concentration of oligodeoxynucleotide ends (one 5' and one 3' end) translates to a higher ligation frequency catalyzed by ligase. In proximity extension, the increased local concentration of oligodeoxynucleotide ends (5-6 base complementary 3' ends from each antibody-oligonucleotide conjugate) translates to a higher rate of extension of the ends by a polymerase. Both methods result in full-length DNA that can be measured with quantitative PCR at levels up to 1000-fold more sensitive than traditional ELISA.

Multiplexed monitoring of protein expression in single cells has been performed in conjunction with single cell transcriptome profiling with the use of antibody-oligonucleotide conjugates. Cells are labeled with conjugates (DNA portion of which contains a target protein-specific barcode) and encapsulated in microfluidic droplets. The conjugates are tagged with a cell-specific barcode followed by next-generation sequencing. As a result, multiplexed protein expression of individual cells is limited only by the number of different antibody-DNA conjugates and the throughput of the DNA sequencing. This is in contrast with flow cytometry or mass cytometry, which have theoretical limits to the numbers of different proteins that can be monitored simultaneously on any given cell. Given that next generation DNA sequencing is still decreasing in cost, it is likely that this type of single-cell proteomics will become increasingly prominent.

These aforementioned advances in protein monitoring are tempered by the inherent difficulty and cost of generating antibody-oligonucleotide conjugates. In addition, there is a need for site-specific conjugation to reduce steric hindrance at complementarity-determining regions, and eliminate the need for stoichiometry optimization and for removal of stabilizing proteins (often included in monoclonal antibody formulations for long-term storage) such as bovine serum albumin (BSA). Amino acid analogs have been suggested for high-efficiency and site-specific conjugation of antigen binding fragments (Fabs) with oligodeoxynucleotides (van Buggenum, et al. (2016) Sci. Reports 6:22675). However, this technology has not been broadly applied, most likely due to the time, cost, and expertise required. Metal binding sites on the Fc domain of antibodies has also been suggested for use in the preparation of antibody-oligonucleotide conjugates (WO 2016/005474 A1). Specifically, PNA, LNA, xylo-LNA-, phosphorothioate-, 2'-methoxy-, 2'-methoxyethoxy-, morpholino- or phosphoramidate-containing oligodeoxynucleotides are functionalized and conjugated to a metal binding site of an antibody. However, the oligonucleotide of this disclosure has no specificity for binding to the antibody.

Selectively binding agents other than antibodies exist. Aptamers are short pieces of single-stranded RNA or DNA that bind to their targets with high selectivity and affinity. Aptamers are obtained by an in vitro evolution method called SELEX (Systematic Evolution of Ligands by EXponential enrichment). SELEX is an iterative process in which a random single-stranded nucleic acid library (~$10^{15}$ different sequences) is mixed with target, target and any bound library are captured and unbound library is washed away, and bound library is amplified with PCR and converted into single-stranded form for a completion of one round of selection. After several rounds of successful selection, the library is enriched for aptamer sequences that bind to the target molecule. SELEX technology has expanded to allow for modified aptamer libraries having increased chemical diversity. For example, alkyne-modified uridine (5-ethynyldeoxyuridine (EdU)) instead of thymidine, has been used in combination with SELEX to prepare a library functionalized with a modification of choice by click chemistry (Pfeiffer, et al. (2018) *Nature Protoc.* 13(5):1153-1180). In addition, display technologies that maintain an unmodified double-stranded DNA physically bound to a chemically modified single-stranded DNA or RNA have been developed. For example, a method termed SELMA (SELection with Modified Aptamers) has been introduced for obtaining heavily chemically modified DNA aptamers (MacPherson, et al. (2011) *Angew Chem. Int. Ed. Engl.* 50:11238-42; Temme, et al. (2013) *Chemistry* 19:17291-95; Temme, et al. (2014) *J. Am. Chem. Soc.* 136:1726-29; Temme & Krauss (2015) *Curr. Protoc. Chem. Biol.* 7:73-92; WO 2018/152470 A1). In SELMA, an unmodified, double-stranded copy of the aptamer remains covalently bound to the single-stranded, chemically modified aptamer. SELMA was successfully used to isolate glycosylated DNA libraries with high affinity (~10 nM) for a glycan-binding antibody, 2G12 (Temme, et al. (2014) *J. Am. Chem. Soc.* 136:1726-29).

As with the oligonucleotides described above, it may be beneficial for a permanent, covalent interaction between aptamer and target, for example for enabling efficient and robust presentation of targets on DNA nanostructures or other nucleic acid-based nanodevices. In addition, covalent coupling of aptamer and target proteins enables the use of harsh conditions for separation and quantification of bound aptamers. In this respect, photo-crosslinking chemistry has been used to evolve aptamers that form a covalent bond with their target (Golden, et al. (2000) *J. Biotechnol.* 81:167-178; Smith, et al. (2003) *Mol. Cell. Proteom.* 2:11-18). The aptamers contain 5-bromodeoxyuridine (BrdU) in place of thymidine. If the aptamer is bound to its target, excitation with a UV laser results in electron transfer from a nearby electron donor, usually an aromatic protein side-chain, to BrdU. Bromide is subsequently ejected and a covalent linkage forms between the radical ion pairs. Photoaptamers were shown to have high specificity, even in complex mixtures (Golden, et al. (2000) *J. Biotechnol.* 81:167-178). Accordingly, methods for site-specific conjugation of aptamers to target proteins is needed.

SUMMARY OF THE INVENTION

In one aspect, this invention provides an aptamer library for identifying a target protein capable of covalent binding to at least one aptamer of said library, wherein said aptamer library is composed of a plurality of aptamers each having at least one nucleotide analog functionalized with an amine-reactive cross-linker. In some embodiments, each of the plurality of aptamers is further bound to an unmodified double-stranded DNA copy of the aptamer. In other embodiments, the at least one nucleotide analog is 5-ethynyldeoxyuridine, 5-ethynyluridine or 2'-modified 5-ethynyluridine. In further embodiments, the amine-reactive cross-linker is an N-hydroxysuccinimide ester or imidoester. A method of using the aptamer library to identify one or more aptamers that covalently bind with, and exhibit specific binding affinity for, a target protein is also provided.

In another aspect, this invention includes an Fc-aptamer conjugate composed of (a) an Fc polypeptide; and (b) an aptamer that specifically binds to a first site on the Fc polypeptide, the aptamer comprising at least one nucleotide analog functionalized with an amine-reactive cross-linker, wherein the Fc polypeptide and aptamer are conjugated via the amine-reactive cross-linker of the aptamer and a primary amine at a second site on the Fc polypeptide proximal to the first site on the Fc polypeptide. In some embodiments, the aptamers are RNA aptamers or DNA aptamers. In other embodiments, the at least one nucleotide analog is 5-ethynyldeoxyuridine, 5-ethynyluridine, 2'-modified-5-ethynyluridine, a triazole-modified deoxyuridine, or a triazole-modified uridine. In further embodiments, the amine-reactive cross-linker is an N-hydroxysuccinimide ester or imidoester. In yet other embodiments, the Fc polypeptide further includes at least a portion of a variable region sequence. In still other embodiments, the aptamer has the nucleotide sequence AGCGCGGAACCGXGCCXGGC (SEQ ID NO:1), XAACGCARXAAGCGAG (SEQ ID NO:2), or CAAXGGCAACAXGCACACAGA (SEQ ID NO:3), wherein at least one X is a nucleotide analog functionalized with an amine-reactive cross-linker. A method for preparing the Fc-aptamer conjugate is also provided.

In a further aspect, this invention provides an aptamer that specifically binds to an Fc region of mouse IgG1 or IgG2, wherein said aptamer has the nucleotide sequence AGCGCGGAACCGXGCCXGGC (SEQ ID NO:1) or XAACGCARXAAGCGAG (SEQ ID NO:2), or an Fc region of a human IgG1, wherein said aptamer has the nucleotide sequence CAAXGGCAACAXGCACACAGA (SEQ ID NO:3), wherein at least one X is a nucleotide analog. In one embodiment, the at least one nucleotide analog is 5-ethynyldeoxyuridine, 5-ethynyluridine, 2'-modified-5-ethynyluridine, a triazole-modified deoxyuridine, or a triazole-modified uridine. In another embodiment, the nucleotide analog further includes an amine-reactive cross-linker. A kit containing the aptamer and optionally an amine-reactive cross-linker is also provided.

In yet a further aspect, this invention includes a phosphoramidite having the structure of Formula I:

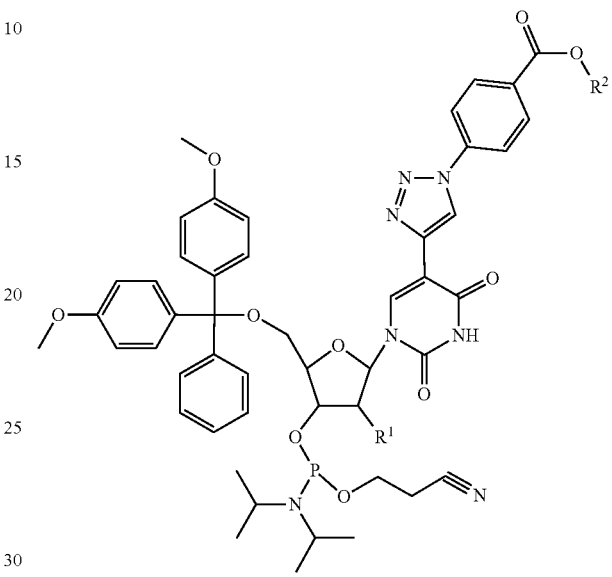

Formula I wherein $R^1$ is H, O-methyl, dimethyl, fluoro, amino, C-allyl, arabinofluoro, methylene, difluoromethylene or a protecting group; and $R^2$ is a protecting group. A kit and method for producing an amine-reactive nucleic acid molecule using the phosphoramidite are also provided.

DETAILED DESCRIPTION OF THE INVENTION

Figure 1:
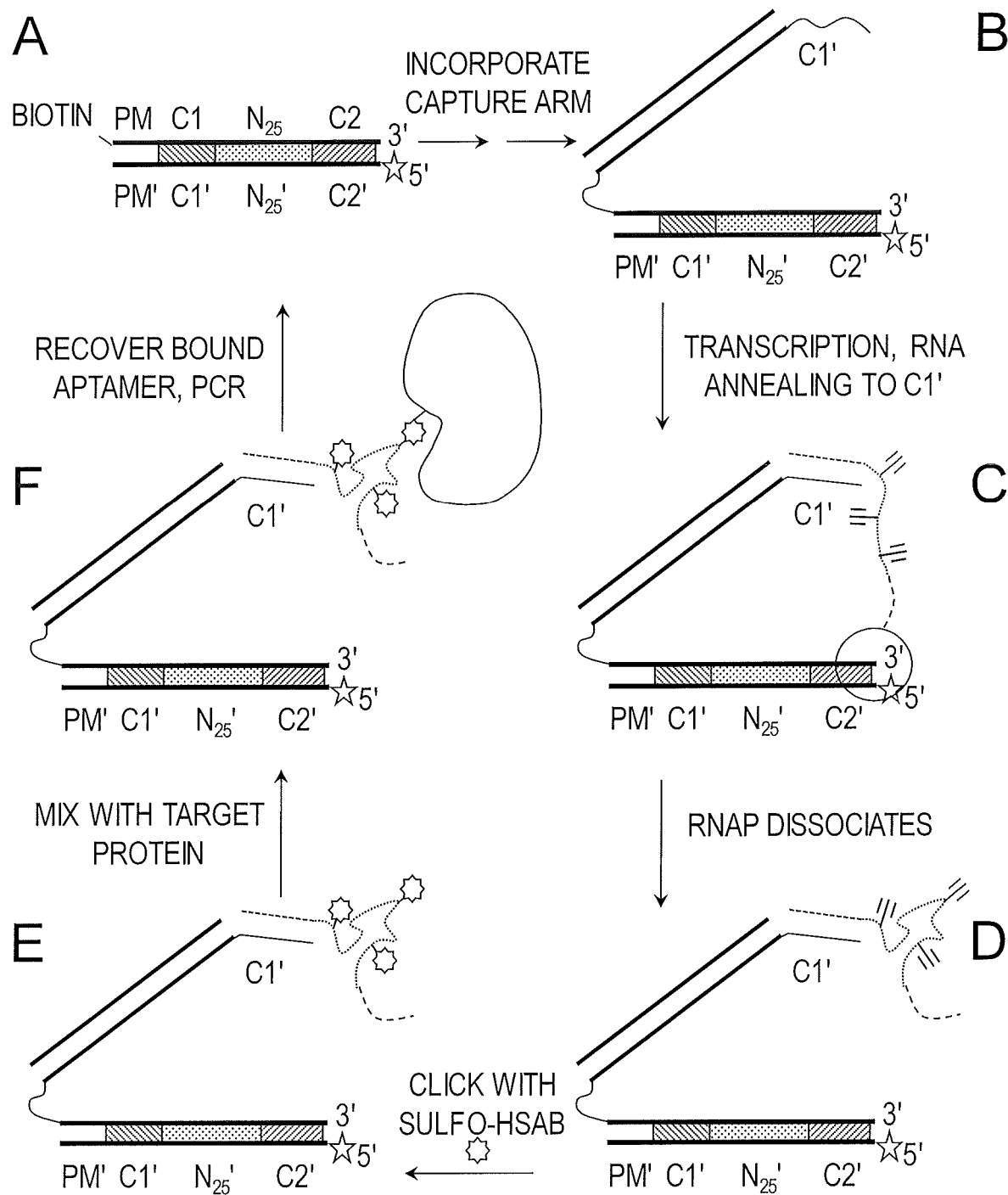
FIG. 1 shows the RNA-SELMA library generation and selection scheme. The library starts as biotinylated double stranded DNA (A). The non-biotinylated strand is isolated followed by annealing and polymerase extension of the capture arm, and annealing of the capture strand rigidifier (B). Transcription with EUTP-containing NTPs is followed by strand capture (C). RNA polymerase subsequently dissociates from the DNA/RNA complex (D) and CuAAC modification of the RNA results in NHS ester functionalization (E). The library is subsequently exposed to a target protein (F). Covalent complexes are then isolated and bound DNA is amplified to regenerate the double-stranded library.

It has now been found that the incorporation of NHS-modified nucleic acids into nucleic acid precursors of RNA and DNA aptamers allows for generation of NHS-modified aptamers of use in the preparation of libraries for identifying molecules that bind covalently to the aptamers as well as in the preparation of protein-aptamer conjugates, in particular Fc-aptamer conjugates. By incorporating at least one alkyne-containing nucleotide analog (5-ethynyldeoxyuridine or 5-ethynyluridine) into the primary sequence of the aptamer, the aptamer can be readily functionalized via click chemistry with an amine-reactive cross-linker such as an NHS ester or imidoester to generate an amine-reactive aptamer, which can be cross-linked to its respective target. Advantageously, when a library of amine-reactive aptamers is used, the library may be recovered and amplified by polymerase chain reaction to regenerate the amine-reactive library for further screening and selection. Furthermore, once a protein-aptamer conjugate of interest has been identified, this invention provides for the use of novel phosphoramidites to facilitate the chemical synthesis of said conjugate. Notably, antibody-aptamer conjugates of this invention find particular use in ultra-sensitive measurements and detection of proteins (e.g., immuno-PCR, proximity ligation, proximity extension, microfluidics-based single-cell proteomics).

Aptamers Libraries. In one aspect, this invention provides for the incorporation of activated esters (specifically N-hydroxysuccinimidyl esters) into DNA or RNA combinatorial libraries and specifically, members of these libraries that exhibit affinity for a target protein and can proficiently react with nucleophiles (specifically primary amines) on a target protein to form a specific covalent bond with the target. Accordingly, the invention provides a combinatorial aptamer library for identifying a target protein capable of covalent binding to at least one aptamer of said library, wherein said library is composed of a plurality of aptamers having at least one nucleotide analog functionalized with an amine-reactive cross-linker.

As used herein, the terms "aptamer" or "nucleic acid aptamer" or "nucleic acid ligand" are used interchangeably to refer to a non-naturally occurring nucleic acid molecule, including RNA or DNA, whose distinct nucleotide sequence determines the folding of the molecule into a unique three-dimensional structure. Notably, the three-dimensional structure allows for the nucleic acid molecule to bind to a target molecule, catalytically change the target, react with the target in a way that modifies or alters the target or the functional activity of the target, covalently attach to the target, and/or facilitate the reaction between the target and another molecule. In certain aspects, the aptamer exhibits specific binding affinity for a target molecule, such target molecule being a three-dimensional chemical structure (other than a polynucleotide) that binds to the aptamer through a mechanism which is independent of Watson/Crick base pairing or triple helix formation. Aptamers of this invention can be prepared as described herein or by conventional chemical synthesis, asymmetric PCR or other PCR-based approaches (e.g., SELEX or SELMA), or polymerase-extension of a primer with EdU-containing dNTPs and removal of the template strand enzymatically (e.g., lambda exonuclease) or physically (e.g., streptavidin magnetic beads and NaOH treatment to remove the non-biotinylated strand).

Aptamers to a given target protein may be identified from a combinatorial aptamer library (e.g., $10^8$-$10^{15}$ molecules), which have a degenerate or random sequence and can further include fixed sequences flanking the degenerate sequence. In some embodiments, the random region is 20 to 100, or 20 to 90, or 20 to 80, or 20 to 70, or 20 to 60, or 20 to 50, or 20 to 40, or 30 to 100, or 30 to 90, or 30 to 70, or 30 to 60, or 30 to 50, or 30 to 40 nucleotides in length. In some embodiments, each aptamer is 20 to 100, or 20 to 90, or 20 to 80, or 20 to 70, or 20 to 60, or 20 to 50, or 30 to 100, or 30 to 90, or 30 to 80, or 30 to 70, or 30 to 60, or 30 to 50, or 40 to 100, or 40 to 90, or 40 to 80, or 40 to 70, or 40 to 60, or 40 to 50 nucleotides in length. In some embodiments, each aptamer includes a fixed region at the 5' end of the aptamer. In some embodiments, the fixed region at the 5' end of each aptamer is at least 10, at least 15, at least 20, at least 25 or at least 30 nucleotides in length, or 5 to 30, 10 to 30, 15 to 30, 5 to 20, or 10 to 20 nucleotides in length. In some embodiments, each aptamer includes a fixed region at the 3' end of the aptamer. In some embodiments, the fixed region at the 3' end of the aptamer is at least 10, at least 15, at least 20, at least 25 or at least 30 nucleotides in length, or 5 to 30, 10 to 30, 15 to 30, 5 to 20, or 10 to 20 nucleotides in length. An exemplary fixed region at the 5' end of the aptamer has the sequence CCGGGCTTTGTGTCACTT (SEQ ID NO:4). An exemplary fixed region at the 3' end of the aptamer has the sequence GCTCGTTCTCCTTCCCTCTCCTATAGTGAGTCGTAT-TACAGTTG (SEQ ID NO:5).

In accordance with the present invention, aptamers of a combinatorial library have at least one nucleotide analog functionalized with an amine-reactive cross-linker. In certain embodiments, the nucleotide analog is an alkyne-substituted nucleotide analog, e.g., 5-ethynyldeoxyuridine, 5-ethynyluridine, or 2'-modified 5-ethynyluridine, which has been functionalized with the amine-reactive cross-linker via cycloaddition reaction. For the purposes of this invention, a "2'-modified 5-ethynyluridine" refers to a 5-ethynyluridine with a modification at the 2' position, which includes, but is not limited to, 2'-O-methyl, 2'-dimethyl, 2'-fluoro, 2'-amino, 2'-C-allyl, 2'-arabinofluoro, 2'-methylene, 2'-difluoromethylene. and the like. See Beigelman, et al. (1995) *J. Biol. Chem.* 270(43):25702-8.

In certain aspects, the amine-reactive cross-linker is a N-hydroxysuccinimide (NHS) ester or imidoester.

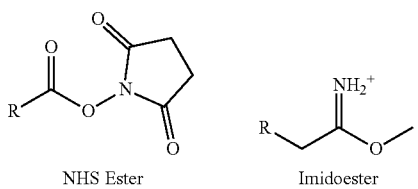

NHS Ester    Imidoester

Exemplary amine-reactive cross-linkers include, for example, NHS-ASA (N-hydroxysuccinimidyl-4-azidosaliucylic acid), sulfo-NHS-ASA, sulfo-NHS-LC-ASA, SASD (sulfosuccinimidyl-2-(p-azidosalicylamido)ethyl-1,3'-dithiopropionate), HSAB (N-hydroxysuccinimidyl-4-azidobenzoate), sulfo-HSAB (N-hydroxysulfosuccinimidyl-4-azidobenzoate), SANPAH (N-succinimidyl-6-(4'-azido-2'-nitrophenylamino)hexanoate), sulfo-SANPAH (sulfosuccinimidyl-6-(4'-azido-2'-nitrophenylamino) hexanoate), ANB-NOS (N-5-azido-2-nitrobenzoyloxysuccinimide), SAND (sulfosuccinimidyl-2-(m-azido-o-nitrobenzamido)-ethyl-1,3'-dithiopropionate), SADP (N-succinimidyl-4(4-azidophenyl)1,3'-dithiopropionate), sulfo-SADP, sulfo-SAPB (sulfosuccinimidyl 4-(p-azidophenyl) butyrate), SAED (sulfosuccinimidyl 2-(7-azido-4-methylcoumarin-3-acetamide)ethyl-1,3'-dithiopropionate), sulfo-SAMCA (sulfosuccinimidyl 7-azido-4-methylcoumain-3-acetate), pNPDP (p-nitrophenyl diazopyruvate), or PNP-DTP (p-nitrophenyl-2-diazo-3,3,3-trifluoropropionate).

Cycloaddition reactions of use in conjugating the amine-reactive cross-linker to a nucleotide analog are known in the art and include, but are not limited to, a Copper-catalyzed azide-alkyne cycloaddition (CuAAC) click chemistry reaction, Ruthenium-Catalyzed Azide-Alkyne Cycloaddition click chemistry reaction, Zinc-Catalyzed Azide-Alkyne Cycloaddition click chemistry reaction, or Copper-free strain promoted azide-alkyne cycloaddition click chemistry reaction. Such reactions can be performed in a variety of solvents, including aqueous mixtures, compositions comprising water and/or aqueous mixtures, and a variety of organic solvents including alcohols, dimethyl sulfoxide (DMSO), dimethylformamide (DMF), tert-butyl alcohol (TBA or tBuOH; also known as 2-methyl-2-propanol (2M2P)), and acetone. In some embodiments, the reaction is a CuAAC click chemistry reaction performed in a milieu comprising a copper-based catalyst such as copper sulfate ($CuSO_4$), tetrakis(acetonitrile)copper(I)hexafluorophosphate (($Cu(CH_3CN)_4$]$PF_6$), tetrakis(acetonitrile)copper(I) triflate ($Cu(CH_3CN)_4$]OTf, copper acetate ($C_4H_6CuO_4$), copper bromide (BrCu) or copper iodide (CuI) and an accelerating ligand such as 2-[4-({bis[(1-tert-butyl-1H-1,2,3-triazol-4-yl)methyl]amino}methyl)-1H-1,2,3-triazol-1-yl] acetic acid (BTTAA), (1-(4-methoxybenzyl)-1-H-1,2,3-triazol-4-yl)methanol (MBHTM), or tris-hydroxypropyltriazolylmethylamine (THPTA).

By way of illustration, a combinatorial library of aptamers may be generated by incorporation of an alkyne-substituted nucleotide analog (e.g., 5-ethynyldeoxyuridine or 5-ethynyluridine) during synthesis of the aptamers and subsequent addition of HSAB or sulfo-HSAB with CuAAC click chemistry. To mitigate the effect of chemical modification on the enzymatic amplification of nucleic acids, preferably a display technology is used, wherein each aptamer of the plurality of aptamers is bound to an unmodified double-stranded DNA copy of the aptamer. See, e.g., WO 2018/152470 A1. For the purposes of this invention, an "unmodified double-stranded DNA" means that the double-stranded DNA molecule does not include a nucleotide analog.

A target protein that covalently binds to one or more aptamers in a combinatorial aptamer library of this invention is identified by (a) contacting the target protein with the aptamer library composed of a plurality of aptamers having at least one nucleotide analog functionalized with an amine-reactive cross-linker, wherein aptamers having an increased affinity to the target relative to other aptamers in the aptamer library can be partitioned from the remainder of the aptamer library; and (b) selecting from the aptamer library one or more aptamers that covalently bind with, and exhibit specific binding affinity for, the target protein. The step of selecting one or more aptamers bound to the target protein can be achieved by partitioning the aptamer-target protein complex from the remainder of the aptamer library using, e.g., a solid support (e.g., bead) bound to the target molecule or aptamer (e.g., as in traditional SELEX), an antibody bound to the target protein. Once selected, the aptamers with increased affinity for the target protein can be amplified to yield a ligand-enriched mixture of aptamers. This process may include multiple rounds to further refine the affinity of the selected aptamers.

In accordance with this invention, an aptamer binding at an epitope that is proximal to a primary amine will readily form a covalent bond with the target protein. As such, the method provides for the identification of an aptamer-target protein complex that (1) includes a target protein with the capacity to covalently bind to the aptamer, i.e., the target protein has a primary amine available nearby for conjugation, and (2) includes an aptamer that has a specific binding affinity for the target protein. It is recognized that affinity interactions are a matter of degree; however, in this context, the "specific binding affinity" of an aptamer or the ability of an aptamer to "specifically bind" to its target means that the aptamer binds to its target in a noncovalent manner with a much higher degree of affinity than it binds to other, non-target, components in a library or sample. Specificity may be determined by several factors, including the pH of the reaction, the type of NHS-ester modification included in the library, the linker length between the NHS ester and the nucleic acid library, steric constraints imposed by the aptamer and the chemical environment around the NHS-ester group.

"Target" or "target protein" refers herein to any protein upon which an aptamer can act in a desirable manner. In certain embodiments, a target protein of this invention is a peptide, glycoprotein, hormone, receptor, antigen, or antibody, which has at least one nucleophile (specifically a primary amine) to form a specific covalent bond with the aptamer. A "target protein" may include a protein that is known to have a biological function, and in some cases, is a protein that has a biological function in a disease or disorder.

Fc-Aptamer Conjugates. Antibody-oligonucleotide conjugates are of particular use in the treatment of disease and in a number of ultra-sensitive protein measurement and detection methods (e.g., immuno-PCR, proximity ligation, proximity extension, microfluidics-based single-cell proteomics). While such conjugates can be prepared via surface amine modification, site-specific conjugation is limited thereby resulting in multiple conjugates per antibody, general instability and interference with epitope binding.

Using the aptamer library and screening method of this invention, aptamers specific for the Fc domain of mouse IgG1 were identified. In particular, using a mouse monoclonal IgG1 anti-streptavidin antibody as the initial bait, an enriched pool of aptamers was identified and subsequently screened using a different mouse IgG1 monoclonal antibody to select for aptamers that bind to conserved parts of the antibody subclass, i.e., the Fc region of the antibody. Advantageously, the Fc region-selective aptamers were covalently bound to the mouse IgG1 via a nearby lysine. Using a similar approach, aptamers specific for the Fc domain of human IgG1 were identified. Using this approach, the conjugation reaction is specific and limited to two conjugations per antibody, thereby providing better signal-to-noise and a lower detection limit. Furthermore, the preparation of conjugates can be vastly simplified given that any antibody of interest can be covalently bound to the Fc-specific aptamers of this invention. Moreover, exogenous sequences (e.g., sequences for proximity extension reactions or barcodes) can be readily attached at permissible points on the covalent aptamer enabling the conjugation of user-defined sequences with antibodies. The simplest attachment method is incorporation of an exogenous sequence to either end of the aptamer sequence during oligonucleotide synthesis. Using this approach, aptamers conjugated to the Fc domains of mouse, rat, rabbit, sheep, goat, pig, guinea pig and human immunoglobulins are achieved.

Accordingly, this invention provides an Fc-aptamer conjugate composed of (a) an Fc polypeptide; and (b) an aptamer that specifically binds to a first site on the Fc polypeptide, the aptamer comprising at least one nucleotide analog functionalized with an amine-reactive cross-linker, wherein the Fc polypeptide and aptamer are conjugated via the amine-reactive cross-linker of the aptamer and a primary amine at a second site of the Fc polypeptide proximal to the first site of the Fc polypeptide.

As used herein, the terms "Fc region," "Fc domain" and "Fc polypeptide" are used interchangeably to refer to the portion of a native immunoglobulin formed by the respective Fc moieties of its two heavy chains. As used herein, the term "Fc polypeptide" refers to a portion of a single immunoglobulin (Ig) heavy chain wherein the Fc domain does not comprise an Fv domain. In certain embodiments, an Fc domain begins in the hinge region just upstream of the papain cleavage site and ends at the C-terminus of the antibody. Accordingly, a complete Fc domain includes at least a hinge domain, a $CH_2$ domain, and a $CH_3$ domain. In certain embodiments, an Fc domain includes at least one of: a hinge (e.g., upper, middle, and/or lower hinge region) domain, a $CH_2$ domain, a $CH_3$ domain, a $CH_4$ domain, or a variant, portion, or fragment thereof. In other embodiments, an Fc domain includes a complete Fc domain (i.e., a hinge domain, a $CH_2$ domain, and a $CH_3$ domain). In one embodiment, an Fc domain includes a hinge domain (or portion thereof) fused to a $CH_3$ domain (or portion thereof). In another embodiment, an Fc domain includes a $CH_2$ domain (or portion thereof) fused to a $CH_3$ domain (or portion thereof). An Fc domain herein generally refers to a polypeptide including all or part of the Fc domain of an immunoglobulin heavy chain.

The Fc domain may be derived from an immunoglobulin of any species including, but not limited to, a mouse, rat, rabbit, sheep, goat, pig, guinea pig and human and/or any subtype including, but not limited to, IgG1, IgG2 (IgG2a or IgG2b), IgG3, IgG4, IgD, IgA, IgE, or IgM antibody, the sequences of which are well-known in the art. For example, the amino acid sequence of mouse IgG1, mouse IgG2a, mouse IgG2b, human IgG1 and rabbit Ig heavy chain constant region are found in FIG. 1 of Nagaoka & Akaike (2003) Protein Engineer. 16(4):243-245). Further, a human IgG1 constant region can be found at Uniprot P01857. Moreover, the Fc domain of human IgG1 with a deletion of the upper hinge region can be found in Table 2 of WO 2016/025642. The term "Fc polypeptide" encompasses both native Fc and Fc variant molecules described in the art.

In certain aspects, the Fc polypeptide of the Fc-aptamer conjugate further includes at least a portion of a variable region sequence (i.e., Fv regions). In this respect, the Fc polypeptide may be a part of a larger polypeptide, e.g., a full-length IgG, a minibody, a mono Fc fusion protein, a bispecific antibody, a dAb-Fc, an scFv-Fc, a half antibody, an scDiabody-CH3, and the like.

The aptamer component of the Fc-aptamer conjugate is characterized by specifically binding to a first site on the Fc polypeptide, i.e., the epitope. The aptamer may be an RNA aptamer or DNA aptamer, which may optionally be modified to include exogenous sequences as described elsewhere herein. In accordance with the conjugate of this invention, the aptamer has at least one nucleotide analog (e.g., 5-ethynyldeoxyuridine, 5-ethynyluridine, 2'-modified 5-ethynyluridine, triazole-modified deoxyuridine, or triazole-modified uridine) functionalized with an amine-reactive cross-linker, such as an N-hydroxysuccinimide ester or imidoester, thereby allowing for covalent bonding of the aptamer to a primary amine located at a second site on the Fc polypeptide, wherein the second site is proximal to the first site (epitope) on the Fc polypeptide. The term "proximal" is defined as a point closer to the point of origin or other reference point than a "distal" site. In this respect, a primary amine (e.g., a lysine) located two, three, four or five amino acid residues or within a radius of less than 10 nm, 5 nm or 1 nm from the epitope located on the Fc polypeptide may be considered "proximal" to the epitope, whereas a primary amino located, e.g., 20 amino acid residues or outside of a radius of 10 nm from the epitope may be considered "distal."

An exemplary aptamer sequence that binds to a first site on the Fc polypeptide of mouse IgG1 (and optionally mouse IgG2a and mouse IgG2b) has at least the nucleotide sequence AGCGCGGAACCGXGCCXGGC (SEQ ID NO:1) or XAACGCARXAAGCGAG (SEQ ID NO:2), wherein R is A or G, and at least one X is a nucleotide analog (e.g., 5-ethynyldeoxyuridine, 5-ethynyluridine, 2'-modified 5-ethynyluridine, a triazole-modified deoxyuridine, or a triazole-modified uridine) that is functionalized with an amine-reactive cross-linker. When not a nucleotide analog, X may be uridine (U), deoxyuridine (dU) or thymidine (dT).

An exemplary aptamer sequence that binds to a first site on the Fc polypeptide of human IgG1 has at least the nucleotide sequence CAAXGGCAACAXGCACACAGA (SEQ ID NO:3), wherein at least one X is a nucleotide analog (e.g., 5-ethynyldeoxyuridine, 5-ethynyluridine, 2'-modified 5-ethynyluridine, a triazole-modified deoxyuridine, or a triazole-modified uridine) that is functionalized with an amine-reactive cross-linker. When not a nucleotide analog, X may be U, dU or dT.

The Fc-aptamer conjugates of this invention can be prepared by contacting the Fc polypeptide, or larger polypeptide containing the same (e.g., an antibody) with the aptamer so that the aptamer specifically binds to a first site on the Fc polypeptide and reacts, via the amine-reactive cross-linker, with a primary amine at a second site of the Fc polypeptide proximal to the first site of the Fc polypeptide. The conjugate thus prepared can be used as is or further purified, e.g., using protein A or protein G magnetic beads, or using a secondary antibody. Alternatively, the conjugate can be purified by precipitation with, e.g., ammonium sulfate. Notably, the aptamer of an antibody-aptamer conjugate prepared in accordance with this method does not interfere with epitope binding thereby reducing any change in antibody specificity for the antibody's cognate epitope. In addition, because the aptamer binds to the Fc region, which is common to antibodies of a species and subtype, the conjugation reaction can be carried out with any antibody in that same species and subtype, independent of antigen binding specificity. As such, the time and cost associated with antibody labeling is significantly reduced.

Fc-Specific Aptamers and Kits. This invention also provides an aptamer and kit containing the same, wherein said aptamer specifically binds to the Fc domain of a mouse IgG1 and/or IgG2 antibody and has the nucleotide sequence AGCGCGGAACCGXGCCXGGC (SEQ ID NO:1) or XAACGCARXAAGCGAG (SEQ ID NO:2), or specifically binds to the Fc domain of a human IgG1 and has the nucleotide sequence CAAXGGCAACAXGCACACAGA (SEQ ID NO:3), wherein at least one X is a nucleotide analog. Preferably, the nucleotide analog is 5-ethynyldeoxyuridine, 5-ethynyluridine, 2'-modified 5-ethynyluridine, or a triazole-modified deoxyuridine, or a triazole-modified uridine (e.g., prepared via solid phase synthesis using the phosphoramidite in Formula I). When not a nucleotide analog, X may be U, dU or dT. In some embodiments, the aptamer is conjugated to an amine-reactive cross-linker as described herein. Alternatively, the aptamer may be provided without an amine-reactive cross-linker. In some embodiments, the kit includes the aptamer without the amine-reactive cross-linker and therefore may further include the amine-reactive cross-linker as a separate component, as well as reagents and instructions for carrying out the cycloaddition reaction. In other embodiments, the kit includes solvents or buffers and instructions for conjugating the aptamer to an Fc polypeptide or antibody. Quantities of the above reagents suitable for performing up to 5, 6, 7, 8, 9, or 10 or more reactions can be provided.

Figure 5:
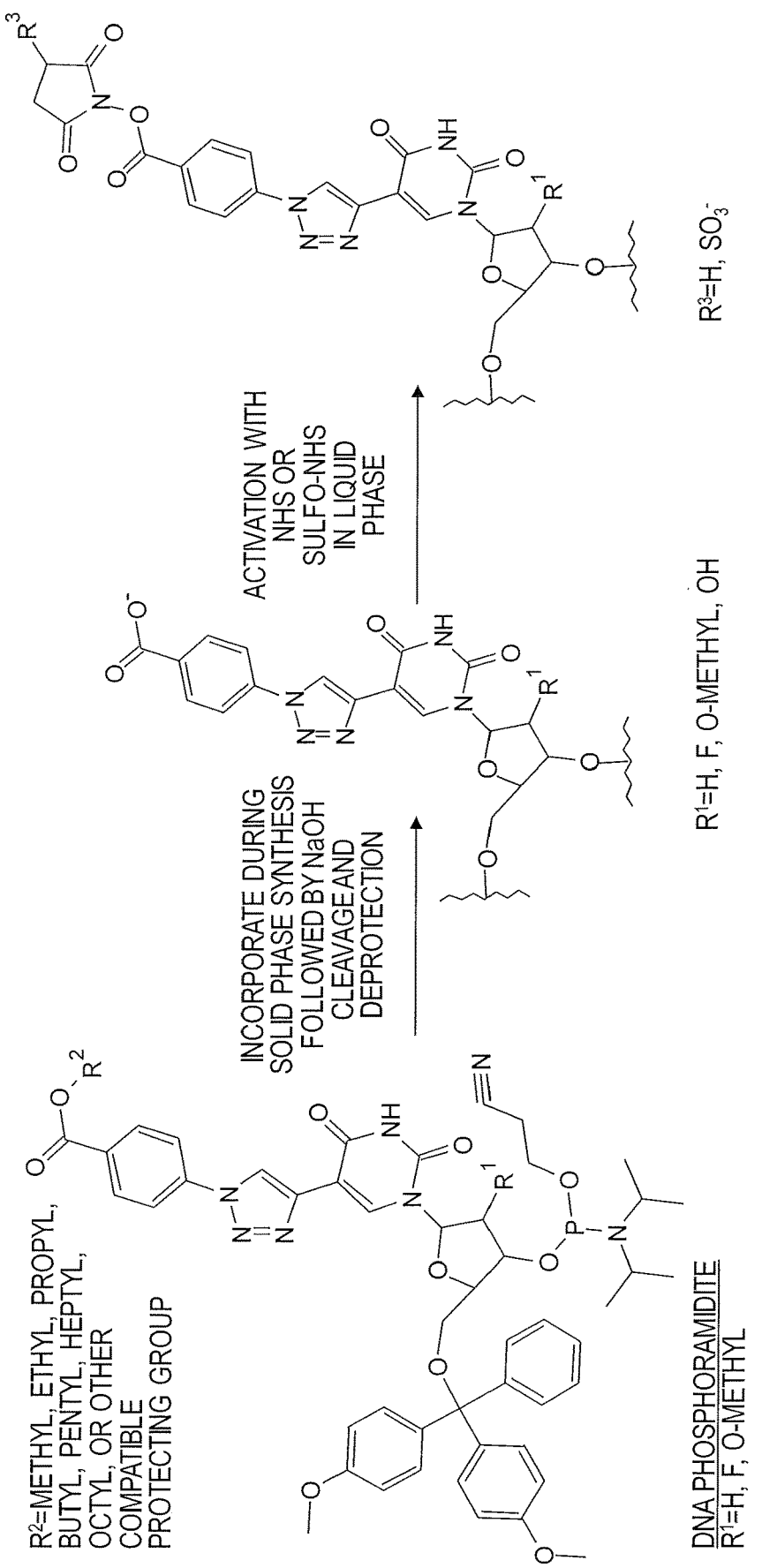
FIG. 5 shows the incorporation of a phosphoramidite of this invention into a nucleic acid molecule, deprotection of the same with NaOH and activation with NHS or sulfo-NHS.

Phosphoramidites. While chemical synthesis of NHS ester-modified aptamers can be achieved by incorporating a 5-ethynyluracil-containing phosphoramidite in solid phase and subsequently carrying out copper-catalyzed azide-alkyne cycloaddition with HSAB or sulfo-HSAB in liquid phase, CuAAC is oxygen-sensitive thereby requiring special handling and large quantities of nucleic acid can inhibit the CuAAC reaction. Therefore, this invention further provides a triazole-modified uridine phosphoramidite for use in the chemical synthesis of an NHS-modified aptamer. In particular, the inventive uridine phosphoramidite analog is modified at the C5 position with a triazolyl derivative of a benzoate ester. The benzoate ester can be formed from short chain alcohols (e.g., methanol, ethanol, butanol, or propanol), which are stable to the solid phase oligonucleotide synthesis conditions and can be cleaved during the deprotection step using sodium hydroxide. The benzoate is then free to be activated with NHS or sulfo-NHS ester for the generation of the NHS-modified aptamer (FIG. 5).

Accordingly, another aspect of this invention is a phosphoramidite of Formula I:

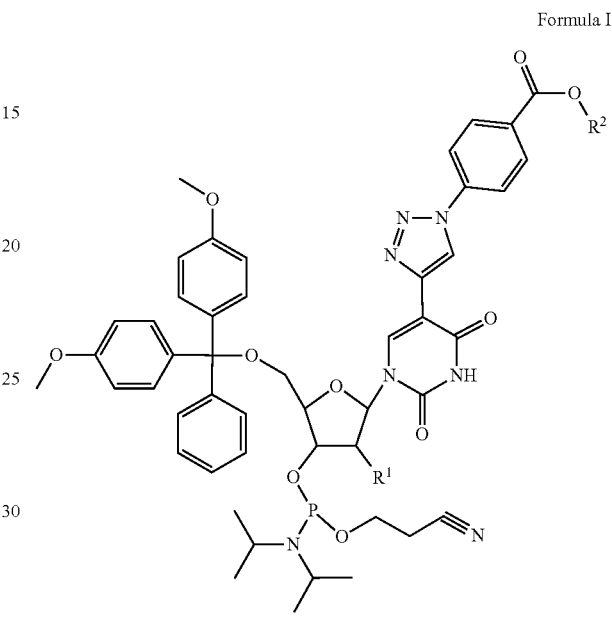

Formula I wherein $R^1$ is H, O-methyl, dimethyl, fluoro, amino, C-allyl, arabinofluoro, methylene, difluoromethylene or a protecting group, such as O-tert-butyldimethylsilyl (TBS), 0-triisopropylsilyloxymethyl (TOM), 2'-bis(2-Acetoxyethoxy)methyl (ACE), thiomorpholine-4-carbothioate (TC), or other suitable protecting group used in RNA or DNA oligonucleotide synthesis; and $R^2$ is a protecting group, in particular an alkyl, wherein said alkyl may be a branched or linear alkyl of 1 to 16 carbon atoms. Exemplary alkyls include, for example, methyl, ethyl, propyl, butyl, isobutyl, pentyl, hexyl, heptyl, octyl, 2-ethyl-hexyl, hexadecyl, or the like.

The phosphoramidite of Formula I may be prepared as outlined in Scheme 1 and may be used in the preparation of an amine-reactive aptamer or any other amine-reactive nucleic acid molecule (see FIG. 5). In this respect, the present invention further provides a method for preparing an amine-reactive nucleic acid molecule by incorporating a triazole-modified deoxyuridine or triazole-modified uridine into the sequence of a nucleic acid molecule using the phosphoramidite of Formula I, e.g., during chemical synthesis; deprotecting the nucleic acid molecule, in particular the benzoate ester with a base such as sodium hydroxide; and contacting the deprotected nucleic acid molecule with an amine-reactive cross-linker, e.g., an NHS or sulfo-NHS ester cross-linker as described herein.

For the purposes of this invention, a "triazole-modified deoxyuridine" or "triazole-modified uridine" incorporated into the sequence of a nucleic acid molecule (e.g., an aptamer or other oligonucleotide) refers to a nucleotide analog having the structure of Formula II:

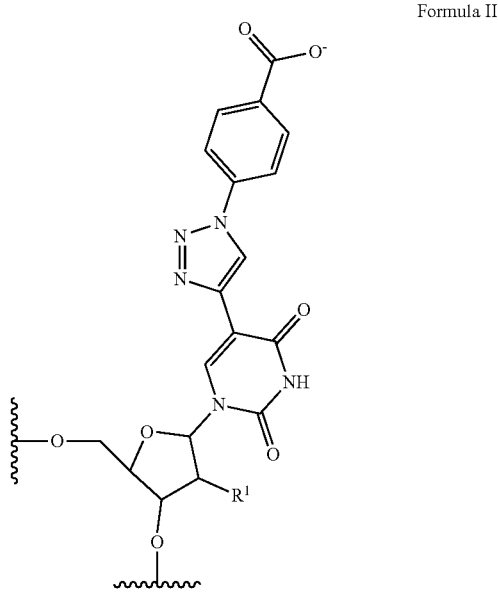

Formula II wherein $R^1$ is H, OH, O-methyl, dimethyl, fluoro, amino, C-allyl, arabinofluoro, methylene, or difluoromethylene.

To facilitate the preparation of an amine-reactive nucleic acid molecule, the present invention further provides a kit containing the phosphoramidite of Formula I, and optionally dNTPs or rNTPs, one or more buffer solutions, sodium hydroxide, and/or an amine-reactive cross-linker. The kit may further include instructions for solid phase synthesis of the nucleic acid molecule, deprotection with sodium hydroxide, and reaction with an amine-reactive cross-linker.

The following non-limiting examples are provided to further illustrate the present invention.

Example 1: Materials and Methods

Materials. All enzymes, streptavidin, streptavidin magnetic beads, denatured bovine serum albumin (BSA) and natural nucleotide triphosphates used in the study were purchased from New England Biolabs. The cloning kit sold under the tradename TOPO TA CLONING® kit and non-denatured BSA (rnase-free) were purchased from ThermoFisher Scientific. All oligonucleotides were purchased from Integrated DNA Technologies. Ethynyluridine triphosphate (EUTP) was purchased from Jena Biosciences. Sulfo-HSAB (N-hydroxysulfosuccinimidyl-4-azidobenzoate) was purchased from GBiosciences. Chemicals, electrophoresis reagents and equipment were purchased from VWR, Sigma and Bio-Rad.

RNA-SELMA Library Construction. Library construction began with PCR of an 87-base aptamer library (Table 1) using a biotinylated forward primer (85 pmol), isodC-containing reverse primer (80 pmol), 5 pmol template library, polymerase (4 units, sold under the tradename VENT® (exo) DNA polymerase) and 200 µM each dNTP in a 200 µL reaction.

TABLE 1

| PCR component | Sequence (5'->3') |
|---|---|
| Random library | CCGGGCTTTGTGTCACTTNNNNNNNNNNNNNNNN NNNNNNNNNNNGCTCGTTCTCCTTCCCTCTCCTA TAGTGAGTCGTATTACAGTTG (SEQ ID NO: 6) (N:15%/28%/29%/28%:A/G/C/T) |
| Biotinylated T7 forward primer | 5'Biotin-CAACTGTAATACGACTCACTATAG GAGA (SEQ ID NO: 7) |
| IsodC reverse primer | 5'isodC-CCGGGCTTTGTGTCACTT (SEQ ID NO: 8) |
| Capture strand* | gctcgttctccttccctctccTTTTTTTTTTCA ACACCACAGACCAGTATACCCAGAAATGACGCA AGCATAGACAAACGATTTAGACATGAGTGCCCC ACACAACGAACAAGCTTTTTTTTTA (SEQ ID NO: 9)-X-CAACTGTAATACGACTCACTATAG GAGA (SEQ ID NO: 10) |
| Capture strand rigidifier | GCTTGTTCGTTGTGTGGGGCACTCATGTCTAAA TCGTTTGTCTATGCTTGCGTCATTTCTGGGTAT ACTGGTCTGTGGTGAA (SEQ ID NO: 11) |
| Unmodified 17 forward primer | CAACTGTAATACGACTCACTATAGGAGA (SEQ ID NO: 12) |
| Unmodified Reverse primer | CCGGGCTTTGTGTCACTT (SEQ ID NO: 13) |

*rigidifier binding site underlined and capture sequence in lowercase letters.
X, hexaethylene glycol spacer Thermal cycling was one cycle at 95° C. for 60 seconds followed by 6 cycles of: 95° C. for 30 seconds, 57° C. for 30 seconds, and 72° C. for 10 seconds. The 200 µL PCR product was incubated with 40 units of exonuclease I and incubated for 30 minutes at 37° C. to digest unused primer. Twenty-five µL of 4 M NaCl and 5 µL 500 mM EDTA were added to the 200 µL PCR product, which was then incubated with 0.28 mg hydrophilic streptavidin magnetic beads on a rotator for 30 minutes. The beads were washed with 150 µL, 125 µL and 100 µL wash buffer (20 mM Tris pH 8.0, 500 mM NaCl) with transfer to a fresh tube after each wash, and incubated with 40 µL 100 mM NaOH for 4 minutes. The supernatant was mixed with 4 µL 1.0 M HCl and 1 µL 1.0 M Tris pH 8.0 for neutralization. Twenty-three µL was added to a new 50 µL reaction containing the capture arm primer (40 pmol) and 5 µL 10× buffer sold under the tradename THERMOPOL® in a volume of 48 µL. The reaction was heated to 95° C. for 60 seconds followed by 57° C. for 60 seconds. One µL Bst 2.0 polymerase sold under the tradename WARMSTART® (8 units) and 1 µL dNTPs (10 mM each) was added, and the reaction was incubated at 60° C. for 90 seconds. The reaction was cooled briefly on ice and loaded onto a spin column with a resin sold under the tradename SEPHADEX® G-50, which was equilibrated with 20 mM Tris pH 8.0, 4 mM MgSO$_4$. The column was subsequently centrifuged to buffer-exchange the library and 14 µL of the buffer-exchanged library was combined with 2 µL T7 RNA polymerase buffer and 10 pmol capture arm rigidifier (1 µL of a 10 µM solution). The mixture was incubated at 50° C. for 5 minutes to facilitate annealing of the rigidifier and incubated with 0.1 mg streptavidin magnetic beads to remove biotinylated contaminants. To the supernatant, 2 µL EUTP-containing NTPs (5 mM each NTP, EUTP replacing UTP), 0.2 µL 1 M DTT and 5 units T7 RNA polymerase were added and the reaction was incubated at 37° C. for 10 minutes. Ten µL of 1×PBS was added to the reaction followed by immediate buffer-exchange into 1× phosphate-buffered saline (PBS) pH 6.0 using a spin column with a resin sold under the tradename SEPHADEX® G-50.

Copper(I)-Catalyzed Azide-Alkyne Cycloaddition "Click" Reaction. The copper(I)-catalyzed azide-alkyne cycloaddition (CuAAC) reaction was performed as follows: The buffer exchanged library was combined with 3.75 µL of mM THPTA ligand (tris-hydroxypropyltriazolylmethylamine), 1 µL of 25 mM $CuSO_4$ and 6 µL of 25 mM sulfo-HSAB (dissolved just prior) in a capless 0.5 mL tube. To a separate capless tube, 20 µL freshly dissolved sodium ascorbate (250 mM) was added. The tubes were placed in a two-necked pear-shaped flask (25 mL) fixed with rubber septa, 18-gauge needles and tubing to allow the flow of argon into one neck and the flow of circulated argon out of the other neck. Foil was placed over the entire system to minimize light degradation of the sulfo-HSAB. Argon flushing was initiated with high flow rate (~5 L/minute) for 3 minutes followed by low flow rate (150 mL/minute) for 30 minutes. At low flow rate, the exhaust septa/needle were removed and the reaction was initiated by transfer of 1 µL sodium ascorbate from one capless tube to other capless tube containing the library, THPTA, copper and sulfo-HSAB followed by pipette mixing with care taken to minimize the introduction of air from the pipettes into the flask. The reaction was allowed to proceed under low argon flow for 30 minutes. The reaction was then buffer-exchanged twice into 1×PBS pH 7.2 using a spin column with a resin sold under the tradename SEPHADEX® G-50.

Selection. The buffer-exchanged library was immediately exposed to hydrophilic streptavidin magnetic beads for covalent attachment. In round 1 of selection, the library was exposed to 0.2 mg of streptavidin magnetic beads for one hour at room temperature on a rotator. These selection conditions were repeated for rounds 2-8. In rounds 9-12 heat-denatured BSA was included and 0.1 mg streptavidin magnetic beads were used. In rounds 13-16, non-denatured BSA (RNase-free) was included at increasing concentration (5 µM-15 µM) with decreasing reaction time (30 minutes-5 minutes) and streptavidin bead amount (0.1-0.02 mg). The beads were washed with 150 µl and 100 µL of wash buffer (20 mM Tris pH 8.0, 500 mM NaCl) resuspended with 30 µL elution buffer (20 mM Tris pH 8.0, 5% nonionic detergent sold under the tradename TWEEN®-20, 150 µg/mL BSA, 50 mM NaCl) and heated at 95° C. in a dry bath incubator for 3 minutes. The supernatant was added to a PCR mix containing 70 pmol biotinylated forward primer, 70 pmol isodC reverse primer, 200 µM each dNTP and 1× buffer sold under the tradename THERMOPOL® buffer in a total volume of 230 µL. Thirty µL was removed to which 0.6 units polymerase sold under the tradename VENT® (exo) DNA polymerase was added and distributed to three tubes which were immediately subjected to thermal cycling. PCR reactions were retrieved at varying cycle intervals and run on 2% agarose and visualized with ethidium bromide to determine the optimal cycle number for recovery of the library. Then, 4 units of polymerase sold under the tradename VENT® (exo) DNA polymerase was added to the remaining 200 µL reaction and the PCR was allowed to proceed to the optimal cycle number. Library was regenerated as with the initial library to initiate another selection round. Following the 16 rounds of selection, the library was amplified with unmodified forward and reverse primers for cloning into plasmid PCR2.1 using the cloning kit sold under the tradename TOPO TA CLONING® kit. Clones were obtained with blue-white colony screening, the plasmids isolated and sequenced using M13 forward and reverse primers.

Binding Studies. For initial assays of library and clone covalent binding, crude RNA samples were used. Briefly, double-stranded DNA PCR products were generated using the biotinylated forward primer and isodC reverse primer and the total library or isolated clone plasmid as template. The PCR product was used directly in a transcription reaction containing EUTP-containing NTPs (0.5 µM each), T7 RNA polymerase in 1×T7 RNA polymerase buffer supplemented with 10 mM DTT. Crude RNA products were buffer-exchanged into PBS pH 6.0 with a spin column with a resin sold under the tradename SEPHADEX® G-50 and a portion (100 ng) was modified with sulfo-HSAB as described above before the addition of the appropriate amount of RNA for the assay (5 nM final concentration). For detailed characterization of clone 4, a large amount of EU-containing RNA was polyacrylamide gel electrophoresis (PAGE)-purified. Approximately 10 ng was modified with sulfo-HSAB. The appropriate amount of streptavidin was mixed with aptamer (~0.5 nM) and the reaction was allowed to proceed for 1 hour in endpoint determination experiments. Reactions were quenched by addition of 1% SDS followed by immediate thermal denaturation at 98° C. for 3 minutes after which Tris pH 8.0 was added to a final concentration of 100 mM and addition of sodium dodecyl sulfate (SDS) loading buffer (1× concentration 6% glycerol, 1% SDS, 20 mM Tris pH 8.0, xylene cyanol dye (trace)). In time-point experiments, reactions were stopped at 3-minute intervals by the above method. For selectivity experiments, aptamer (0.5 nM) was incubated with and without 10 nM streptavidin and varying concentration of non-denatured BSA. In all gel shift experiments, visualization was accomplished by annealing a 21-base DNA strand (20 nM) labeled with a fluorophore (sold under the tradename IRDYE® 700) in SDS loading buffer. After an initial denaturation step of 98° C. for 3 minutes, samples were cooled to 70° C. followed by slow cooling (0.3° C./second) to 37° C. Samples were loaded onto 10% acrylamide SDS-PAGE mini-gels (19:1 acrylamide:bisacrylamide) and electrophoresed at 200 V for 12 minutes. Gels were imaged and quantified with a system sold by LI-COR under the tradename ODYSSEY®.

Example 2: SELMA-Based Selection of Bioconjugation-Proficient RNA Aptamers to Streptavidin A schematic of the library generation and selection strategy is presented in FIG. 1. The library was generated by the RNA SELMA method, in which a "capture arm" is added to a typical double-stranded DNA library composed of a T7 RNA polymerase promoter and a random region (25 bases) flanked by two constant regions. When transcription occurs, the capture arm is capable of annealing to the nascent RNA before it dissociates from the T7 RNA polymerase. This is aided by the addition of a non-natural analog isodC at the 5' end of the template strand. In accordance with one aspect of this invention, the uridine triphosphate was replaced with 5-ethynyluridine triphosphate in the transcription reaction to incorporate a functional group amenable to copper-catalyzed alkyne-azide cycloaddition, or "click chemistry." After transcription, the library was modified with N-hydroxysulfosuccinimidyl-4-azidobenzoate (sulfo-HSAB) via click chemistry. Notably, the sulfo-HSAB provided the azide component, and the presence of Cu(I) catalyst and Cu(I)-stabilizing ligand tris(3-hydroxypropyltriazoylmethyl) amine (THPTA) in a low-oxygen, argon atmosphere resulted in efficient NHS ester functionalization of the library. Moreover, of importance, the reaction was carried out at a pH of 6.0, which minimized hydroxyl ion-dependent hydrolysis of the ester.

The library was then exposed to streptavidin magnetic beads, the bound library was amplified by PCR and the library regenerated for the next round of selection. During the 7$^{th}$ round of selection, the PCR cycle number required to reach optimal recovery decreased from 14 to 10, indicating that the library was enriched with covalent binders for streptavidin. During selection cycle 9-12, heat-denatured BSA (1-5 μM) was included at the binding step to counter-select non-specific binders. A further 4 rounds of selection were performed with non-denatured BSA competitor (5-15 μM) and increased stringency. A table summarizing selection conditions and PCR recovery is found in Table 2. After the 16$^{th}$ round of selection, the library was cloned and 10 isolates were sequenced and characterized.

TABLE 2

| Round | Conditions | PCR Cycle # for recovery |
|---|---|---|
| 1 | 0.2 mg beads, 1 hour | 14 |
| 2 | 0.2 mg beads, 1 hour | 14 |
| 3 | 0.2 mg beads, 1 hour | 14 |
| 4 | 0.2 mg beads, 1 hour | 14 |
| 5 | 0.2 mg beads, 1 hour | 14 |
| 6 | 0.2 mg beads, 1 hour | 14 |
| 7 | 0.2 mg beads, 1 hour | 10 |
| 8 | 0.2 mg beads, 1 hour | 10 |
| 9 | 0.1 mg beads, 30 minutes, 1 μM BSA (denatured) | 12 |
| 10 | 0.1 mg beads, 30 minutes, 1 μM BSA (denatured) | 12 |
| 11 | 0.1 mg beads, 30 minutes, 5 μM BSA (denatured) | 12 |
| 12 | 0.1 mg beads, 30 minutes, 5 μM BSA (denatured) | 12 |
| 13 | 0.1 mg beads, 30 minutes, 5 μM BSA (native) | 13 |
| 14 | 0.1 mg beads, 30 minutes, 5 μM BSA (native) | 13 |
| 15 | 0.1 mg beads, 30 minutes, 15 μM BSA (native) | 14 |
| 16 | 0.02 mg beads, 5 minutes, 15 μM BSA (native) | 16 |

Aptamers and aptamer complexes were detected by annealing a fluorophore-labeled DNA strand to the RNA under SDS-denaturing conditions, which do not substantially effect oligonucleotide hybridization (Rose, et al. (2002) BioTechniques 33:54-56, 58). SDS-PAGE gel shift assay comparing the library after 16 rounds of selection with a naïve library. In the presence of streptavidin, a shifted band was clearly identified for the selected library but not for the naïve library. To rule out the possibility of other factors in the apparent covalent binding, "mock" modified EU-containing RNAs were prepared in which sulfo-HSAB was omitted from the CuAAC reaction. In this scenario, no gel shift was observed for either the selected or naïve libraries when exposed to 200 nM streptavidin. Lastly, pre-treatment of the sulfo-HSAB-modified selected library with 50 mM Tris pH 8.0 for 20 minutes abolished the band shift whereas addition of Tris after the reaction with streptavidin does not abolish the shifted band. Together, these observations confirm the presence of sulfo-HSAB modification-dependent, covalently reactive RNA aptamers in the library.

From the library, 10 clones were sequenced and characterized. A list of the clone sequences and their covalent binding activity is found in Table 3.

TABLE 3

| Clone | Sequence from random region (aligned) | SEQ ID NO: | Covalent complex? |
|---|---|---|---|
| 10 | CCGGGEAGCCEEAACEGAC--GCGCEE | 14 | + |
| 6 | CCGGGEAGCCEEAACEGAC--GCGCEE | 14 | + |
| 7 | AGGGCAAAAEEEAACEGAC--AAGCEE | 15 | + |
| 3 | AGGGEAAAAEEEAACEGAC--AAGCE- | 16 | - |
| 8 | EGGAAACGCAEEAACEAAC--AAGCEE | 17 | + |
| 5 | --GGGACAGCEEAACEGACGAAAACEE | 18 | + |
| 4 | --GGGACAGCEEAACEGACGAAAACEE | 18 | + |
| 2 | --AGGCACGEAEAACEGACAAACGCEE | 19 | + |
| 9 | AEAACGGCAEEGAGCEEAACEGEAA------- | 20 | + |
| 1 | EAGCACCEAACAEEECEEGAAAEGA | 21 | - |

"E" represents 5-ethynyluridine.

A conserved motif (E/A)EAACE(G/A) was identified from nine of the ten sequences. Clone pairs (4 and 5) and (6 and 10) contained identical sequences. The last sequence (clone 1) did not appear to have any sequence similarity with the other nine clones. Individual clones were characterized by their ability to cause a denaturing gel shift upon incubation with streptavidin (Table 3). Clone 1, which did not contain the conserved motif, did not show observable covalent binding activity. Eight of the 10 clones (2,4,5,6,7,8,9, 10) formed a shifted band in the presence of streptavidin. Clones 6 and 10, which have an identical sequence, showed two bright bands even in the absence of streptavidin, indicating higher-order species most likely resulting from dimerization of the aptamers. However, with streptavidin incubation, a shifted band was evident just below the higher order band and at the top of the gel. It appears that the banding pattern at the top of the gel was of dimers of aptamers with either one or two streptavidin monomers bound. Clone 3, which differs from clone 7 by a deletion of a semi-conserved ethynyluridine as well as a C to E substitution away from the conserved region, did not cause a gel shift while clone 7 did. This observation may be explained by a recent loss of function of clone 3, where mutation late in the selection experiment occurred (most likely during the last amplification step prior to cloning).

Clone 4 was selected for further characterization. An endpoint binding assay was performed in which the aptamer was mixed with varying concentrations of streptavidin and assessed for covalent complex formation by SDS-PAGE gel shift. The binding curve indicated half-maximal covalent complex formation at <10 nM streptavidin. One might expect the covalent reaction to proceed to completion for all functioning aptamers, regardless of target concentration. However, nucleophilic attack by hydroxyl ion is a known side-reaction of NHS esters. Apparently at low streptavidin concentrations (10-20 nM), the aptamer is competitively quenched by hydroxyl ion such that lower reactivity occurs, compared with higher streptavidin concentration.

Figure 2:
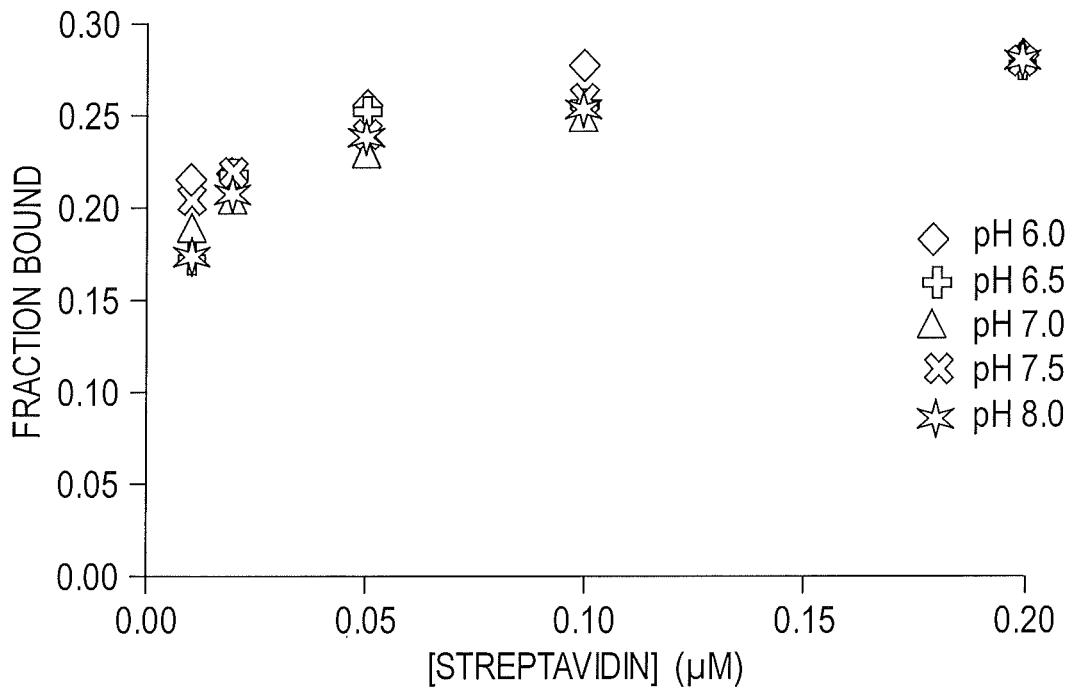
FIG. 2 Shows SDS-PAGE gel shift data for clone 4 at varying pH. Sulfo-HSAB-modified clone 4 was prepared as described in the examples and reacted with increasing concentrations of streptavidin at the designated pH, denatured with SDS and annealed to a fluorophore-conjugated oligonucleotide, electrophoresed on SDS-PAGE and quantified by fluorescence.

NHS ester reactions are typically dependent on pH. Thus, the ability of clone 4 to form a covalent complex was characterized at varying pH (FIG. 2). For all reactions in which a shift was observed, a second more slowly migrating shifted band was also observed, and the relative intensity of the second band increased with increasing pH. The most probable explanation of the second band is the reaction of a single aptamer with two streptavidin monomers (of the functional tetramer). While not wishing to be bound by theory, it is likely that after the initial covalent reaction, a second NHS ester is positioned near an adjacent streptavidin monomer such that it can react with a primary amine from that monomer. Accordingly, the second shifted band was included in the calculation of total reacted aptamer. Similar binding plots were observed at all pH levels tested (6.0-8.0). To determine if initial reaction rates varied with pH, complex formation was measured as a function of time at pH 6.0 and 8.0 and 10 nM streptavidin. Slightly faster rates of reaction were observed at pH 8.0. Therefore, the endpoint data could be explained by slower reaction rate at lower pH for a longer duration (lower quenching rate) and faster reaction rate at higher pH for a shorter duration (higher quenching rate).

Figure 3:
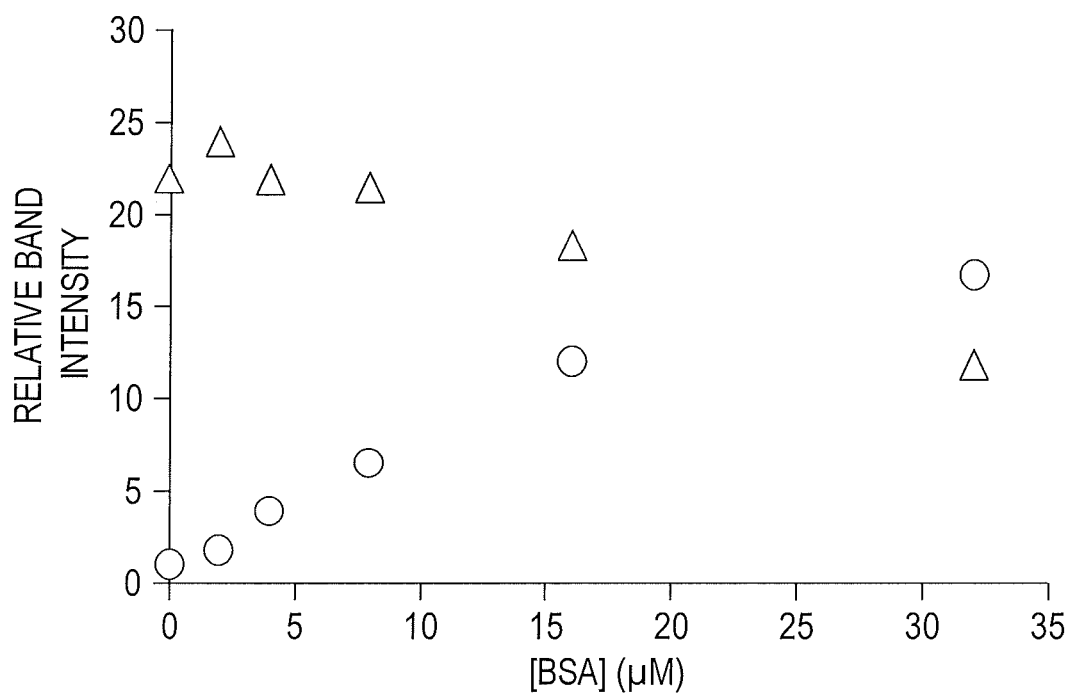
FIG. 3 shows the specificity of clone 4 as determined by BSA competition assay. Increasing concentrations of BSA were included in the reaction of NHS ester-modified clone 4 with streptavidin (10 nM). The plot shows the RNA-streptavidin covalent product (triangles) and RNA-BSA covalent product (circles) as a function of BSA concentration.

Clone 4 was also assessed for reaction specificity. To this end, the NHS ester-modified clone was incubated with varying concentrations of bovine serum albumin (BSA). BSA contains 30-35 lysine residues capable of reaction with NHS esters. In comparison, streptavidin has 12-16 lysine residues capable of reaction with NHS esters. NHS ester-modified clone 4 (~0.5 nM) and streptavidin (10 nM) were incubated with increasing concentrations of BSA (0-32 μM) at pH 7.2. A decrease in the streptavidin-shifted band corresponded with an increase in a slower-migrating BSA-shifted band, with equal band intensities at 8 μM-16 μM BSA, indicating a specificity coefficient of 1000 for streptavidin (FIG. 3).

Example 3: DNA Aptamer-Mouse IgG1 Conjugates

Using chemically modified aptamers, DNA aptamers to the Fc region of mouse IgG1 were generated and shown to form a specific covalent bond with the antibody upon binding. In general, an aptamer library armed with a covalently reactive group, i.e., an amine-reactive cross-linker, was generated for conjugation of Fc-selective aptamers to primary amines (lysines or N-termini) in the Fc region of mouse IgG1. By functionalizing the library with NHS esters, even low-affinity specific binding can result in covalent reactivity (if the aptamer binding brings an NHS ester into reactive contact with a primary amine on the antibody) thereby increasing the probability that covalently binding aptamers can be isolated for any given Fc fragment.

This labeling strategy has significant advantages over non-specific methods. In particular, steric hindrance of antibody function is minimized if antibody-oligonucleotide conjugates are formed at the Fc domain, away from complementarity determining regions. Further, heterogeneity in the degree of labeling is minimized, obviating the need for high-resolution chromatography. A large excess of DNA can be used for labeling to ensure saturation of two specific conjugation sites per Fc dimer with aptamer. Since the resulting reactions are virtually free of unlabeled antibody, a simple protein precipitation step can be used to remove unconjugated aptamers. Moreover, no genetic manipulation of the antibody is required, thereby minimizing cost.

Figure 4:
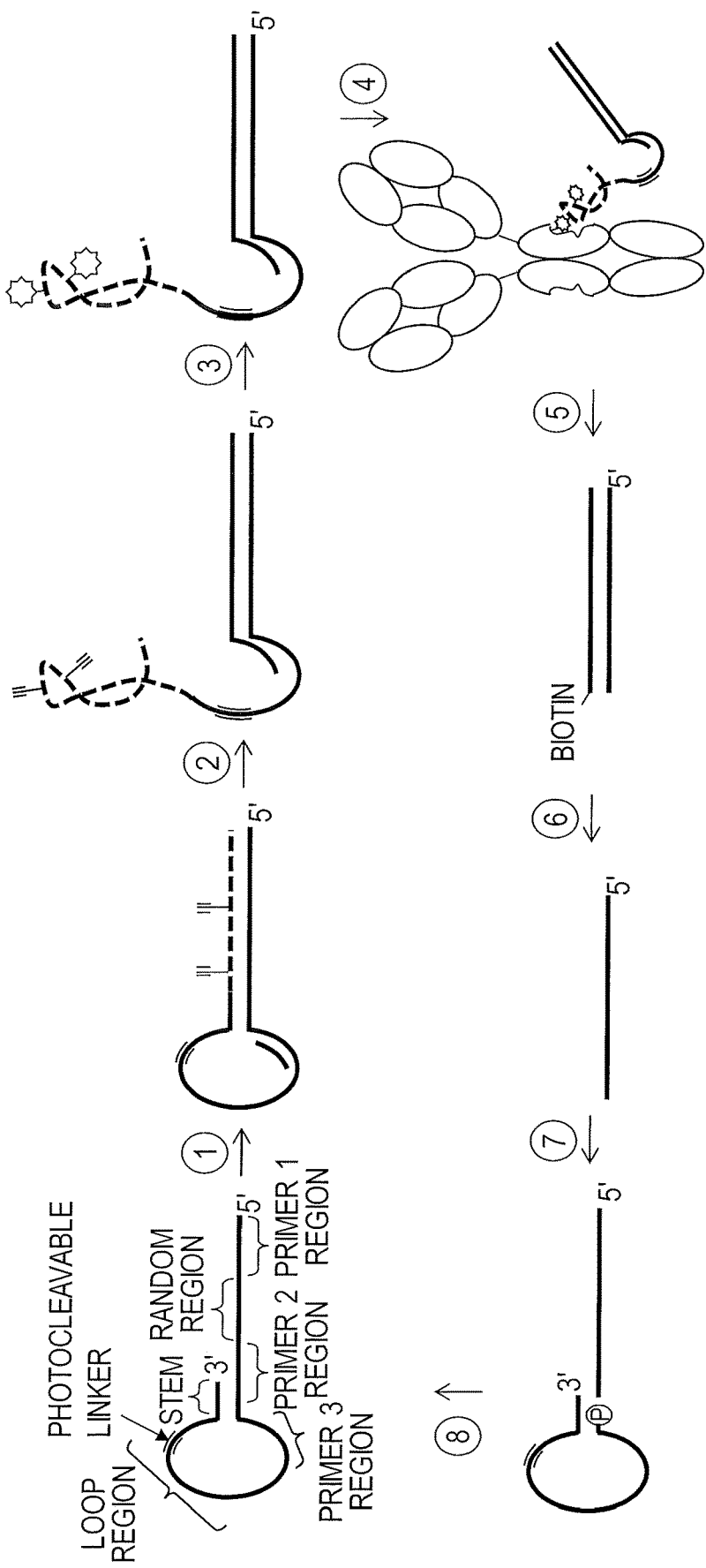
FIG. 4 shows a schematic of the library screening approach for isolating Fc-specific covalent DNA aptamers. Step 1) Enzymatic incorporation of commercially available EdU-triphosphate (replacing thymidine triphosphate) along with natural dATP, dCTP, and dGTP. Step 2) Polymerase-based displacement of the EdU-containing strand. Step 3) CuAAC modification with sulfo-HSAB. Step 4) Exposure of Mouse IgG1 monoclonal antibody (100 nM) to the library. Step 5) Magnetic bead capture of IgG1-aptamer conjugates followed by washing, elution with 350 nm light and amplification of eluted conjugates. Step 6) Isolation of the negative PCR strand. Step 7 and Step 8) Annealing and ligation to a regeneration oligonucleotide to complete a single round of selection.

Similar to the method described in Example 1, a library of DNA aptamers was generated, which incorporated 5-ethynyldeoxyuridine triphosphate (EdU) and addition of azido-NHS ester (sulfo-HSAB) with click chemistry (FIG. 4). The base composition of the library was controlled allowing for 10% ethynyldeoxuridine incorporation (30% each of adenosine, cytosine, guanosine) in the random region (FIG. 4, step 1), resulting in 2-3 modifications per construct, on average. To mitigate the effect of chemical modification on the enzymatic amplification of nucleic acids, SELMA was used, where an unmodified double-stranded DNA copy of the aptamer was physically bound to the modified copy. The library was screened with mouse IgG1 anti-streptavidin using streptavidin beads for recovery. After 4 rounds of selection using a mouse monoclonal IgG1 antibody as bait, enrichment of the library was apparent based on the lowering in PCR cycle number required for efficient amplification of the library from 19 to 15 (FIG. 4, step 5). At this point, the target was changed to a different mouse IgG1 monoclonal antibody to select for binding to conserved parts of the antibody subclass. In rounds 5 and 6, amplification of the eluted library was achieved at 12 PCR cycles.

Assessment of the NHS-modified portion of the library (ssDNA region after step 2, FIG. 4) for covalent binding in excess monoclonal mouse IgG antibody revealed a high degree of conjugation compared to a naïve random library, as determined by SDS-PAGE gel shift assay with fluorescence detection of the DNA. Surprisingly, the library was also reactive with mouse IgG2a and mildly reactive with mouse IgG2b. Also, the selected library showed significant reactivity with the Fc fragment of mouse IgG1 compared with the naïve random library. When an excess of NHS-DNA was reacted with IgG1, a distinct two-phase gel-shift was apparent in a non-reducing gel, in agreement with the occupation of two sites within the Fc dimer. Monitoring the DNA in this reaction showed 2 major bands, again consistent with specific labeling of one or two sites in the dimeric Fc fragment.

Deep sequencing was undertaken to observe individual clone sequences of the library after round 6. Two sequence families made up ~93% of all the reads. More specifically, approximately half had the consensus sequence NMMM-RAGCGCGGAACCGTGCCTGGC (SEQ ID NO:22) and about a third had the consensus sequence GRCMRRRRR-TAACGCARTAAGCGAG (SEQ ID NO:23), wherein R is A or G, M is A or C, and N is A, T, C or G. Accordingly, it was determined that core consensus sequences for binding to the Fc fragment were AGCGCGGAACCGTGCCTGGC (SEQ ID NO:24) and TAACGCARTAAGCGAG (SEQ ID NO:25). The sequences (referred to respectively as clone 1 and 2) contained highly conserved motifs with predicted hairpin structures encompassing two NHS ester modification sites (T bases in the variable region), strongly suggesting a role for these short sequences in covalent reactivity. Clones 1 and 2 were verified to bind to mouse IgG1, IgG2a and to a lesser extent mouse IgG2b, with clone 1 containing a higher bound fraction (40% for mouse IgG1 and IgG2a and 10% for IgG2b) than clone 2 (20% for IgG1 and IgG2a, 2% for IgG2b), consistent with their relative abundance in the deep sequencing data. Reaction of an excess of DNA with IgG1 resulted in the predicted two-phase shift, albeit with higher efficiency for clone 1, again consistent with a higher binding fraction for this sequence. Maximum binding fraction is a parameter typically used to describe aptamers because aptamer folding is never 100% for any given sequence. Notably, 40% and 20% are close to the maximum binding fractions for clone 1 and 2, respectively. Likewise, the $K_D$, or dissociation constant, is a parameter typically determined for aptamers. Because the interaction is irreversible, the $K_D$ could not be determined. However, it was estimated that the antibody concentration at which covalent binding was half-maximal for clone 1 and 2 was ≤10 nM. To determine the minimal reactive sequence of clone 1, 32 bases on the 5' end of clone 1 were removed and random bases were added. Notably, truncated clone 1 still bound with high efficiency to the Fc region of the antibody.

Initially, it was noted that the library exhibited a high degree of variability in conjugation efficiency with different DNA preparations, and exhibited complete inhibition of conjugation when micromolar concentrations of BSA were present in the reaction. Further testing indicated that the reaction was dependent on nanomolar concentrations of copper(II). This dependence could be explained by a variable amount of residual copper remaining in solution after copper-catalyzed click chemistry modification of the DNA library (using 0.8 mM $CuSO_4$), even after the reaction was buffer-exchanged twice with a gel filtration spin column.

Not wishing to be bound by the theory, it was believed that the residual Cu(I) re-oxidized to Cu(II) and aided in covalent reactivity of the library. Inhibition by BSA could be explained by a well-documented high affinity copper binding site on serum albumin that is implicated in copper homeostasis in humans and other mammals. Including a copper concentration higher than that of the BSA recovered covalent reactivity of clone 1. Based on this analysis and the faint shifted band generated by reaction with BSA, the specificity coefficient for clone 1 reaction with IgG1 over BSA in the presence of saturating $CuSO_4$ was estimated to be 500-1000. Copper interactions with DNA are well-documented, and the presence of cationic copper in the complex is likely to reduce electrostatic repulsion between highly anionic DNA and near-neutral Fc fragment. This copper binding site is proposed to exist in IgG in species ranging from rabbit to human, providing a potential simplified path toward further isolation of Fc-specific aptamers for IgGs from other species used for monoclonal production (rat, rabbit, and guinea pig), none of which bind to clones 1 and 2.

Example 4: DNA Aptamer-Rat, -Rabbit and Guinea Pig IgG1 Conjugates

As described in Example 3, DNA aptamer libraries are generated using the DNA display strategy presented in FIG. 4. EdUTP replaces TTP in the polymerase extension of the starting hairpin. Annealing a primer within the hairpin loop and extension with a strand displacing polymerase results in EdU-containing ssDNA connected to dsDNA containing the same sequence of natural nucleotides. CuAAC with sulfo-HSAB is used to modify the library with NHS esters. The modified library is incubated with antibody from either rat, rabbit or guinea pig in the presence of 1 μM copper sulfate and binders recovered by capturing antibody and antibody-library complexes with protein A/G magnetic beads. After washing, bound library is eluted by irradiation of the beads with 350 nm light. The supernatant is removed via a magnetic rack and submitted to PCR amplification. A pilot PCR amplification step is performed with a fraction of the eluted DNA to determine the optimal cycle number for library recovery, and complete recovery at the optimal cycle number is performed in a scaled-up reaction containing the bulk of the eluted DNA. Isolation of the negative DNA strand and ligation to the regeneration oligonucleotide completes one round of selection. Aptamers are expected to be enriched in 6-10 rounds of selection, each requiring a day. Oscillation between different monoclonal antibodies of the same class will select for broad binding specificity as observed in preliminary experiments with mouse IgG1.

Libraries are tested for enrichment for covalent reactivity by SDS-PAGE gel shift assay. If covalent binding is confirmed, deep sequencing is used to identify clones comprising the library. Individual clones are tested for covalent binding activity with a broad panel of monoclonal antibodies. Concentration of antibody yielding half-maximal covalent bond formation is determined (similar to a dissociation constant, a parameter typically determined for aptamers). Lastly, competition assays are performed to determine the selectivity of the aptamer against BSA.

Example 5: Chemical Synthesis of Aptamers

Constructs were obtained in microgram quantities by PCR-based linear amplification in the presence of EdUTP-containing dNTPs to generate click-modifiable aptamers, followed by CuAAC for the generation of NHS ester-modified aptamers. This provides more than enough DNA for gel shift assays, albeit with some impurities. If covalent aptamer-mediated conjugation is to be broadly useful, the synthesis of such modified oligonucleotides must allow for mixtures of thymidine and thymidine analog nucleotides and must be scaled up considerably (0.1 to 1.0 milligram scale). Therefore, modified aptamers are synthesized using phosphoramidite chemistry. There are two potential paths toward chemical synthesis of the sulfo HSAB-modified aptamers. In the first approach, commercially available EdU phosphoramidite is used to synthesize EdU-containing constructs with an oligonucleotide synthesizer, after which CuAAC is performed with sulfo-HSAB in an appropriate buffer to generate the aptamer. In another approach, a 5-triazolyl benzoate methyl ester is incorporated into uridine phosphoramidite for chemical synthesis. The synthetic strategy is presented in Scheme 1.

SCHEME 1

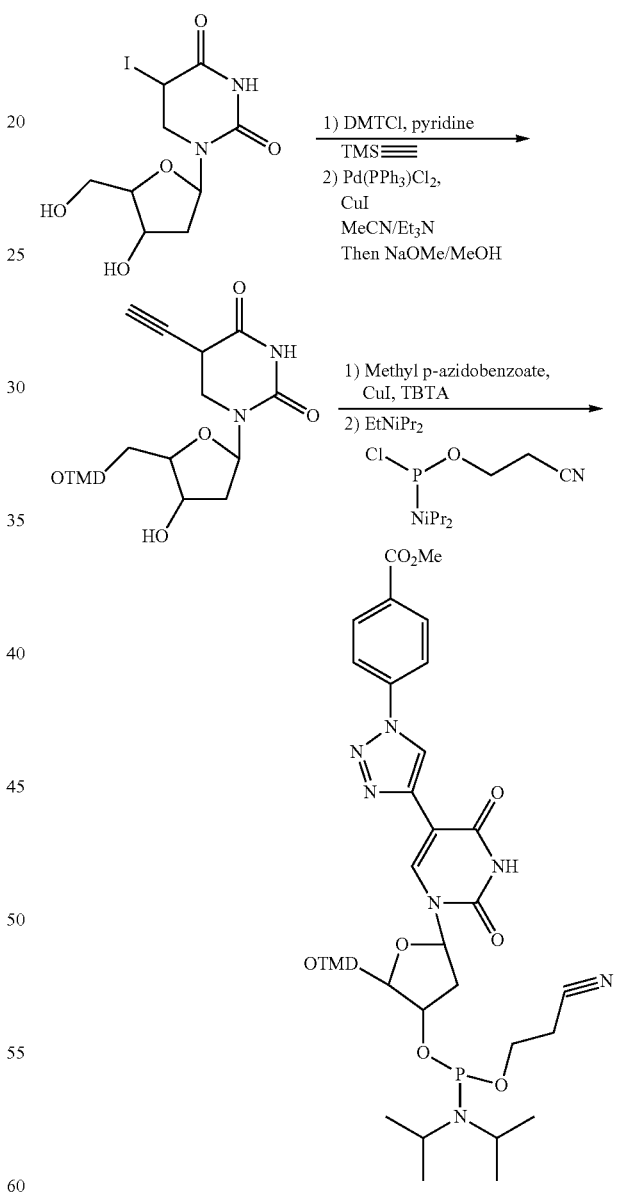

The final product represents the CuAAC product between EdU phosphoramidite and azidobenzoate methyl ester. After oligonucleotide synthesis, deprotection in NaOH will cleave base protecting groups and the methyl ester, and sulfo-NHS functionalization can be performed in the presence of 1-ethyl-3-(3-dimethylaminopropyl)-carbodiimide (EDC), an activator commonly used for NHS functionalization of carboxylic acids. Performing the CuAAC step during synthesis of the phosphoramidite building block circumvents potential difficulties associated with CuAAC of large quantities of DNA, which can sequester copper and render the CuAAC less efficient. Furthermore, the EDC/NHS approach is not sensitive to oxygen thereby simplifying the process for the end user.

What is claimed is:

1. A method for producing one or more aptamers that bind to a target protein comprising
   (a) contacting a target protein with an aptamer library comprising a plurality of aptamers each having at least one nucleotide analog functionalized with an amine-reactive cross-linker;
   (b) selecting from the aptamer library one or more aptamers that covalently bind, and exhibit specific binding affinity for, the target protein; and
   (c) introducing a triazole-modified nucleotide into the sequence of the one or more aptamers that covalently bind, and exhibit specific binding affinity for, the target protein, wherein the triazole-modified nucleotide is introduced into the one or more aptamers by:
      (i) incorporating a phosphoramidite comprising the structure of Formula I:

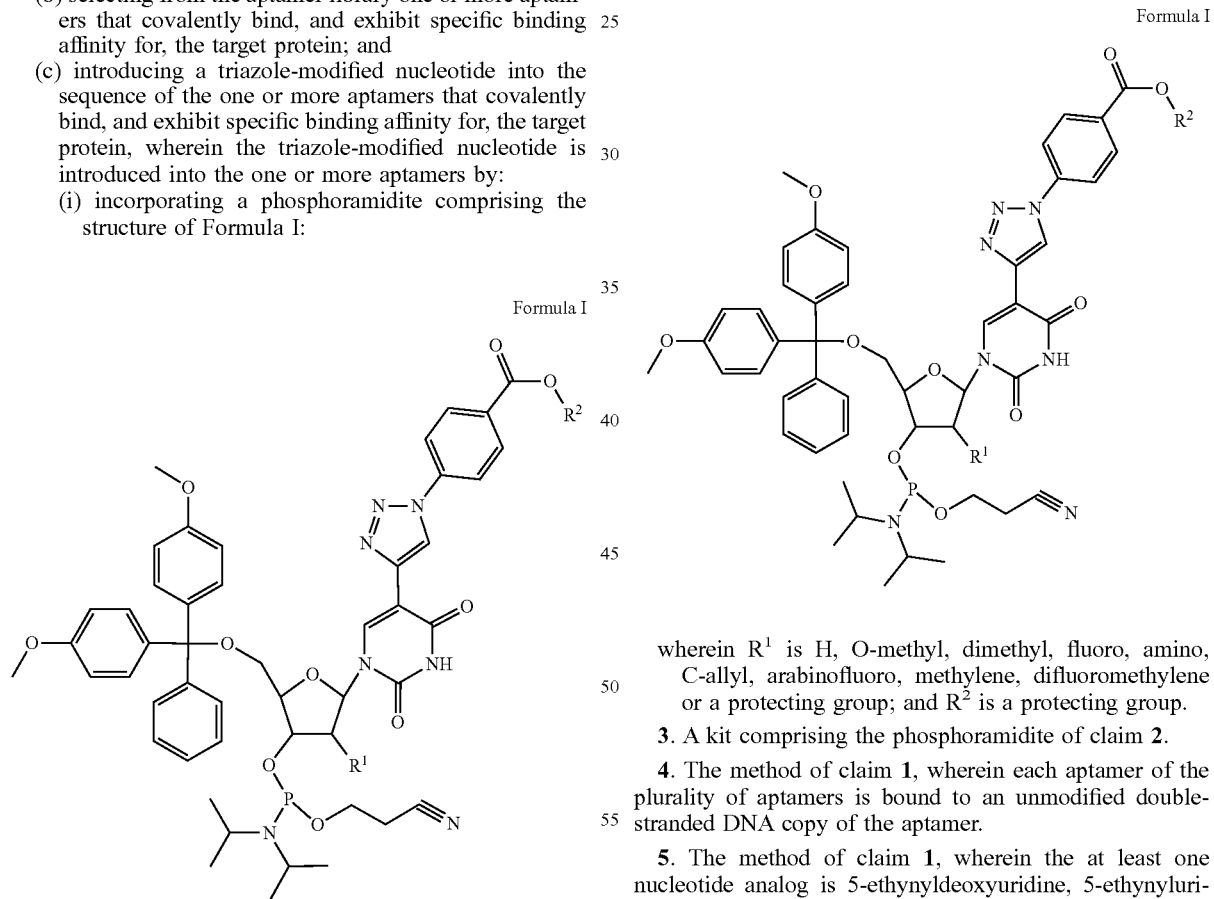

Formula I wherein $R^1$ is H, O-methyl, dimethyl, fluoro, amino, C-allyl, arabinofluoro, methylene, difluoromethylene or a protecting group; and $R^2$ is a protecting group, (ii) deprotecting the aptamers, and
   (iii) activating the deprotected aptamers to form an amine-reactive cross-linker.

2. A phosphoramidite comprising the structure of Formula I:

Formula I wherein $R^1$ is H, O-methyl, dimethyl, fluoro, amino, C-allyl, arabinofluoro, methylene, difluoromethylene or a protecting group; and $R^2$ is a protecting group.

3. A kit comprising the phosphoramidite of claim 2.

4. The method of claim 1, wherein each aptamer of the plurality of aptamers is bound to an unmodified double-stranded DNA copy of the aptamer.

5. The method of claim 1, wherein the at least one nucleotide analog is 5-ethynyldeoxyuridine, 5-ethynyluridine, or 2'-modified 5-ethynyluridine.

6. The method of claim 1, wherein the amine-reactive cross-linker is an N-hydroxysuccinimide ester or imidoester.

* * * * *